US008717019B2

(12) United States Patent
Ookawa

(10) Patent No.: US 8,717,019 B2
(45) Date of Patent: May 6, 2014

(54) MAGNETIC RESONANCE IMAGING APPARATUS AND LOAD CALCULATION METHOD OF A GRADIENT MAGNETIC FIELD GENERATION SYSTEM

(75) Inventor: Masashi Ookawa, Otawara (JP)

(73) Assignees: Kabushiki Kaisha Toshiba, Minato-Ku, Tokyo (JP); Toshiba Medical Systems Corporation, Otawara-Shi, Tochigi-Ken (JP)

( * ) Notice: Subject to any disclaimer, the term of this patent is extended or adjusted under 35 U.S.C. 154(b) by 0 days.

(21) Appl. No.: 13/614,276

(22) Filed: Sep. 13, 2012

(65) Prior Publication Data
US 2013/0009639 A1    Jan. 10, 2013

Related U.S. Application Data

(63) Continuation of application No. PCT/JP2012/064926, filed on Jun. 11, 2012.

(30) Foreign Application Priority Data

Jun. 13, 2011  (JP) ................................ 2011-131385

(51) Int. Cl.
*G01V 3/00*          (2006.01)
(52) U.S. Cl.
USPC ........................................................ 324/307
(58) Field of Classification Search
USPC ................................................ 324/300–322
See application file for complete search history.

(56) References Cited

U.S. PATENT DOCUMENTS

| 6,516,282 B2* | 2/2003 | Hedlund et al. ............... 702/132 |
| 2002/0156595 A1* | 10/2002 | Hedlund et al. ............... 702/132 |
| 2013/0009641 A1* | 1/2013 | Hori et al. ...................... 324/309 |

FOREIGN PATENT DOCUMENTS

| JP | 8-056917 | 3/1996 |
| JP | 2004-357771 | 12/2004 |

OTHER PUBLICATIONS

International Preliminary Report on Patentability in PCT/JP2012/064926 issued Dec. 17, 2013.

* cited by examiner

*Primary Examiner* — Dixomara Vargas
(74) *Attorney, Agent, or Firm* — Nixon & Vanderhye PC

(57) ABSTRACT

According to one embodiment, an MRI apparatus performs magnetic resonance imaging under a gradient magnetic field by providing a gradient magnetic field generation system with electric current so as to apply the gradient magnetic field on an imaging region. This MRI apparatus includes a condition setting unit and a load acquisition unit. The condition setting unit sets imaging conditions of the magnetic resonance imaging. The load acquisition unit acquires information on a waveform of the gradient magnetic field, and calculates respective electric loads for a plurality of frequency bands imposed on the gradient magnetic field generation system in a case of performance of the magnetic resonance imaging, based on the information on a waveform.

19 Claims, 18 Drawing Sheets

MAGNETIC RESONANCE IMAGING APPARATUS AND LOAD CALCULATION METHOD OF A GRADIENT MAGNETIC FIELD GENERATION SYSTEM

CROSS-REFERENCE TO RELATED APPLICATION

This application is a Continuation Application of No. PCT/JP2012/64926, filed on Jun. 11, 2012, and the PCT application is based upon and claims the benefit of priority from Japanese Patent Application No. 2011-131385, filed on Jun. 13, 2011, the entire contents of which are incorporated herein by reference.

BACKGROUND OF THE INVENTION

1. Field of the Invention

Embodiments described herein relate generally to a magnetic resonance imaging apparatus and a load calculation method of a gradient magnetic field generation system.

2. Description of the Related Art

MRI is an imaging method which magnetically excites nuclear spin of an object (a patient) set in a static magnetic field with an RF pulse having the Larmor frequency and reconstructs an image based on MR signals generated due to the excitation. The aforementioned MRI means magnetic resonance imaging, the RF pulse means a radio frequency pulse, and the MR signal means a nuclear magnetic resonance signal.

A gradient magnetic field generation system in an MRI apparatus includes a gradient magnetic field coil which adds spatial positional information to MR signals by applying a gradient magnetic field in an imaging space where an object is set. This gradient magnetic field coil produces heat by being provided with pulse electric current during imaging. A gradient magnetic field generation system has various limitations in terms of the total upper limit of electric power, the respective upper limits of electric power in each channel and the like, and does not have enough ability to endure the maximum electric current in every channel (X axis direction, Y axis direction and Z axis direction) concurrently.

However, in conventional technology, it is difficult to precisely estimate application limits of a gradient magnetic field generation system in terms of electric power according to an imaging sequence.

Therefore, in prior art, initial rise characteristics of a gradient magnetic field coil are calculated by using an ohmic value at "the maximum temperature allowable for the gradient magnetic field coil", imaging conditions are determined in this calculated range, and then the gradient magnetic field coil is driven (see, for example, Patent Document 1).

Although the initial rise characteristics in the aforementioned case are under the worst conditions, the temperature of a gradient magnetic field coil rarely reaches the maximum temperature in actual status of use.

As just described, a gradient magnetic field generation system is safely driven under control of keeping a sufficient margin between actual supplied amount of electric current and the application limit value. That is, the supplied amount of electric current to a gradient magnetic field generation system is controlled so as to surely fall below its application limit value.

[Patent Document 1] Japanese Patent Application Laid-open (KOKAI) Publication No. H08-56917

In the aforementioned conventional technology, though there is an enough margin from its application limit, a gradient magnetic field generation system is sometimes driven more safely than its application limit. If there was an enough margin up to the application limit of a gradient magnetic field generation system, imaging could be performed under more optimized conditions by increasing a slice number by the value corresponding to the margin, for example.

Thus, technology of accurately estimating electric load on a gradient magnetic field generation system in MRI depending on an imaging conditions has been desired in order to perform imaging under more optimized conditions.

DETAILED DESCRIPTION

According to one embodiment, an MRI apparatus performs magnetic resonance imaging under a gradient magnetic field by providing a gradient magnetic field generation system with electric current so as to apply the gradient magnetic field on an imaging region, and includes a condition setting unit and a load acquisition unit. The condition setting unit sets imaging conditions of the magnetic resonance imaging. The load acquisition unit acquires information on a waveform of the gradient magnetic field, and calculates respective electric loads for a plurality of frequency bands imposed on the gradient magnetic field generation system in a case where the magnetic resonance imaging is performed, based on the information on a waveform.

According to another embodiment, the load acquisition unit calculates an electric load on the gradient magnetic field generation system in the case of performance of the magnetic resonance imaging, based on information on frequency of a waveform of the gradient magnetic field, and output the electric load.

According to one embodiment, a load calculation method of a gradient magnetic field generation system includes the steps of:

(a) setting imaging conditions of magnetic resonance imaging under a gradient magnetic field applied by a gradient magnetic field generation system; and (b) calculating an electric load on the gradient magnetic field generation system in the case of performance of the magnetic resonance imaging, based on the imaging conditions.

A magnetic resonance imaging apparatus, a magnetic resonance imaging method, and a load calculation method of a gradient magnetic field generation system according to embodiments of the present invention will be described with reference to the accompanying drawings.

Note that the same reference numbers are given for identical components in each figure, and overlapping explanation is abbreviated.

First Embodiment

Figure 1:
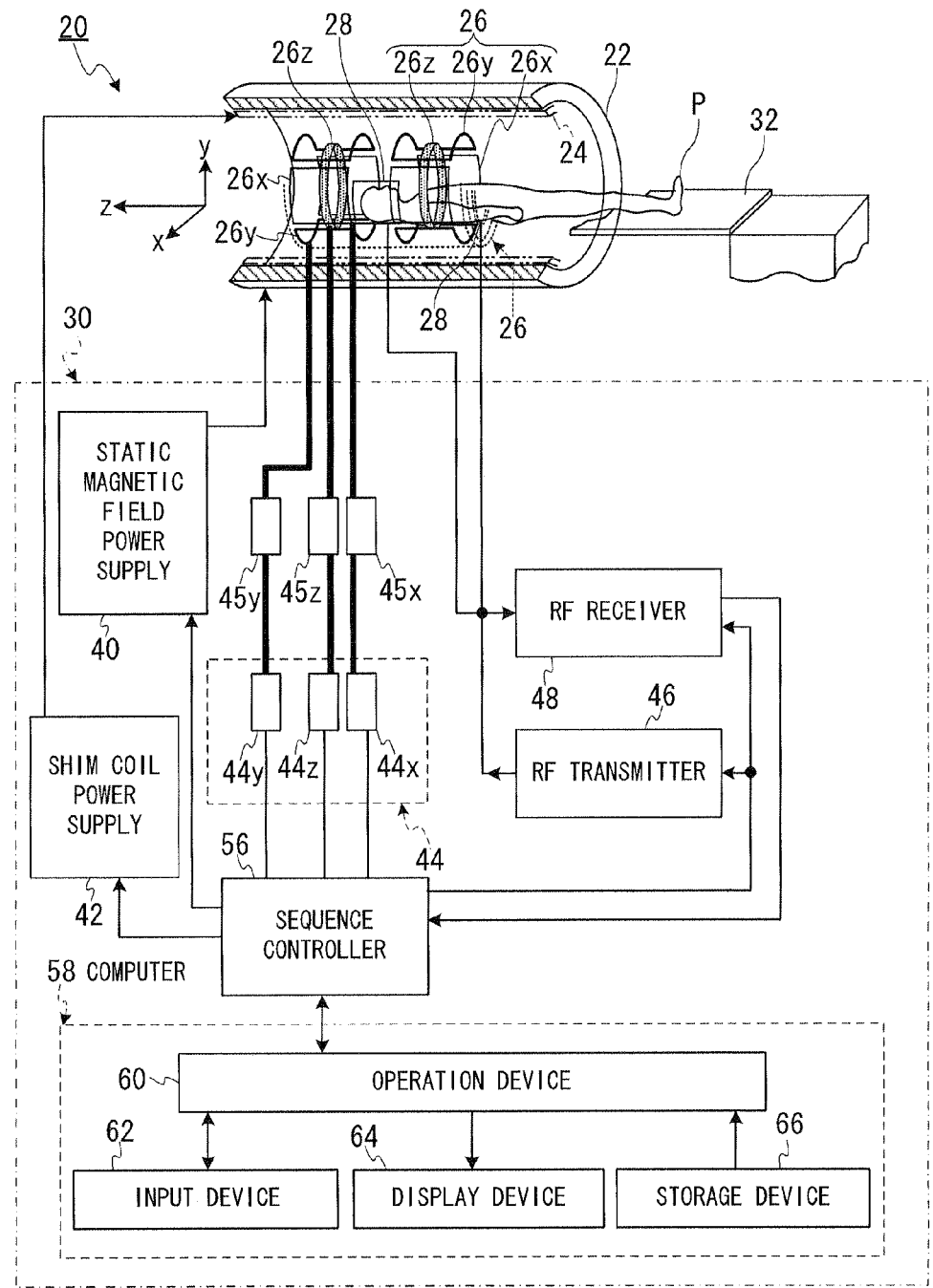
FIG. 1 is a block diagram showing general structure of the MRI apparatus of the first embodiment.

FIG. 1 is a block diagram showing general structure of the MRI apparatus 20 according to the first embodiment.

As shown in FIG. 1, the MRI apparatus 20 includes a cylinder-shaped static magnetic field magnet 22 for generating a static magnetic field, a cylinder-shaped shim coil 24 coaxially-arranged inside the static magnetic field magnet 22, a gradient magnetic field coil 26, RF coils 28, a control system 30, and a bed 32 for placing an object (e.g. a patient) P on it.

Here, as one example, an apparatus coordinate system, whose X axis, a Y axis and a Z axis are perpendicular to each other, is defined as follows.

Firstly, the direction of an axis of the static magnetic field magnet 22 and the shim coil 24 is aligned with the direction which is perpendicular to the vertical direction, and the direction of the axis of the static magnetic field magnet 22 and the shim coil 24 is defined as the Z axis direction.

Additionally, it is assumed that the vertical direction is the same as the Y axis direction. Moreover, the bed 32 is disposed in such a position that the direction of "the normal line of the table plane thereof on which an object is put" is the same as the Y axis direction.

The control system 30 includes a static magnetic field power supply 40, a shim coil power supply 42, a gradient magnetic field power supply 44, EMC (Electro Magnetic Compatibility) filters 45$x$, 45$y$, 45$z$, an RF transmitter 46, an RF receiver 48, a sequence controller 56 and a computer 58.

The gradient magnetic field power supply 44 includes an X axis gradient magnetic field power supply 44$x$, a Y axis gradient magnetic field power supply 44$y$ and a Z axis gradient magnetic field power supply 44$z$.

The computer 58 includes an operation device 60, an input device 62, a display device 64 and a storage device 66.

The static magnetic field magnet 22 is electrically connected to the static magnetic field power supply 40 and generates a static magnetic field in an imaging space by using electric current supplied from the static magnetic field power supply 40.

The aforementioned imaging space means, for example, a space in a gantry in which an object P is placed and to which a static magnetic field is applied. The term gantry refers to a structure having a cylindrical shape, for example, which includes the static magnetic field magnet 22, the shim coil 24, the gradient magnetic field coil 26, and the RF coils 28. For simplicity, FIG. 1 does not show the gantry itself, but shows the static magnetic field magnet 22 and so on in the gantry as components of the gantry.

The imaging region means, for example, at least a part of an acquisition range of MR signals used to generate one image or one set of images, which becomes an image. The imaging region is defined as a part of the imaging space in terms of range and position by an apparatus coordinate system, for example.

The one image or one set of images may be a two-dimensional image or a three-dimensional image. Here, one set of images means, for example, a plurality of images when MR signals of the plurality of images are acquired in a lump in one pulse sequence such as multi-slice imaging.

The "one image" or "one set of image" may be a two-dimensional image or a three-dimensional image. Here, "one set of images" means, for example, a plurality of images when MR signals of the plurality of images are acquired in a lump in one pulse sequence such as multi-slice imaging.

The shim coil 24 is electrically connected to the shim coil power supply 42 and uniforms the static magnetic field with the electric current supplied from the shim coil power supply 42.

The static magnetic field magnet 22 includes a superconductivity coil in many cases. The static magnetic field magnet 22 is electrically connected to the static magnetic field power supply 40 and supplied with electric current from the static magnetic field power supply 40 at excitation. However, once excitation has been made, the static magnetic field magnet 22 is usually isolated from the static magnetic field power supply 40. The static magnetic field magnet 22 may include a permanent magnet which makes the static magnetic field power supply 40 unnecessary.

The gradient magnetic field coil 26 includes an X axis gradient magnetic field coil 26x, a Y axis gradient magnetic field coil 26y and a Z axis gradient magnetic field coil 26z. Each of the X axis gradient magnetic field coil 26x, the Y axis gradient magnetic field coil 26y and the Z axis gradient magnetic field coil 26z is cylinder-shaped and is arranged inside the static magnetic field magnet 22.

The X axis gradient magnetic field coil 26x, the Y axis gradient magnetic field coil 26y and the Z axis gradient magnetic field coil 26z are electrically connected to the X axis gradient magnetic field power supply 44x, the Y axis gradient magnetic field power supply 44y and the Z axis gradient magnetic field power supply 44z, respectively.

The X axis gradient magnetic field power supply 44x, the Y axis gradient magnetic field power supply 44y and the Z axis gradient magnetic field power supply 44z supply electric current to the X axis gradient magnetic field coil 26x, the Y axis gradient magnetic field coil 26y and the Z axis gradient magnetic field coil 26z respectively, so as to generate a gradient magnetic field Gx in the X axis direction, a gradient magnetic field Gy in the Y axis direction and a gradient magnetic field Gz in the Z axis direction in the imaging region.

That is, directions of a gradient magnetic field Gss in a slice selection direction, a gradient magnetic field. Gpe in a phase encode direction and a gradient magnetic field Gro in a readout (frequency encode) direction can be arbitrarily set as logical axises, by combining the gradient magnetic fields Gx, Gy and Gz in the X axis, the Y axis and the Z axis directions of the apparatus coordinate system.

The gradient magnetic fields Gss, Gpe and Gro in the slice selection direction, the phase encode direction and the readout direction are superimposed on the static magnetic field.

The EMC filter 45x is inserted in series in a cable (a bold line part in FIG. 1) which electrically connects the X axis gradient magnetic field power supply 44x to the X axis gradient magnetic field coil 26x, and filters out (reject) extraneous noise. Similarly, the EMC filter 45y is inserted in series in a cable which electrically connects the Y axis gradient magnetic field power supply 44y to the Y axis gradient magnetic field coil 26y, the EMC filter 45z is inserted in series in a cable which electrically connects the Z axis gradient magnetic field power supply 44z to the Z axis gradient magnetic field coil 26z, and the EMC filters 45y and 45z filters out extraneous noise.

The RF transmitter 46 generates RF pulses (RF current pulses) having the Larmor frequency for causing nuclear magnetic resonance based on control information provided from the sequence controller 56, and outputs the generated RF pulses to the transmission RF coil 28.

The RF coils 28 include a whole body coil built in the gantry for transmission and reception of RF pulses and local coils arranged around the bed 32 or the object P for reception of RF pulses.

The transmission RF coil 28 transmits an RF pulse given from the RF transmitter 46 to the object P. The reception RF coil 28 receives an MR signal (a radio-frequency signal) generated due to excited nuclear spin inside the object P by the RF pulse and this MR signal is detected by the RF receiver 48.

The RF receiver 48 generates raw data which are digitized complex number data obtained by performing A/D (analogue to digital) conversion after performing predetermined signal processing such as preamplification, intermediate-frequency conversion, phase detection, low-frequency amplification and filtering to the detected MR signal. The RF receiver inputs the generated raw data to the sequence controller 56.

The operation device 60 performs system control of the MRI apparatus 20 in imaging operation, and its function will be explained later with FIG. 2.

The sequence controller 56 stores control information needed in order to make the gradient magnetic field power supply 44, the RF transmitter 46 and the RF receiver 48 drive. The aforementioned control information includes, for example, sequence information describing operation control information such as intensity, impression period and impression timing of the pulse electric current which should be impressed to the gradient magnetic field power supply 44.

The sequence controller 56 generates the gradient magnetic fields Gx, Gy and Gz in the X axis, the Y axis and the Z axis directions and RF pulses by driving the gradient magnetic field power supply 44, the RF transmitter 46 and the RF receiver 48 according to a predetermined sequence stored. Additionally, the sequence controller 56 receives the raw data of an MR signal inputted from the RF receiver 48, and input the raw data to the operation device 60.

Figure 2:
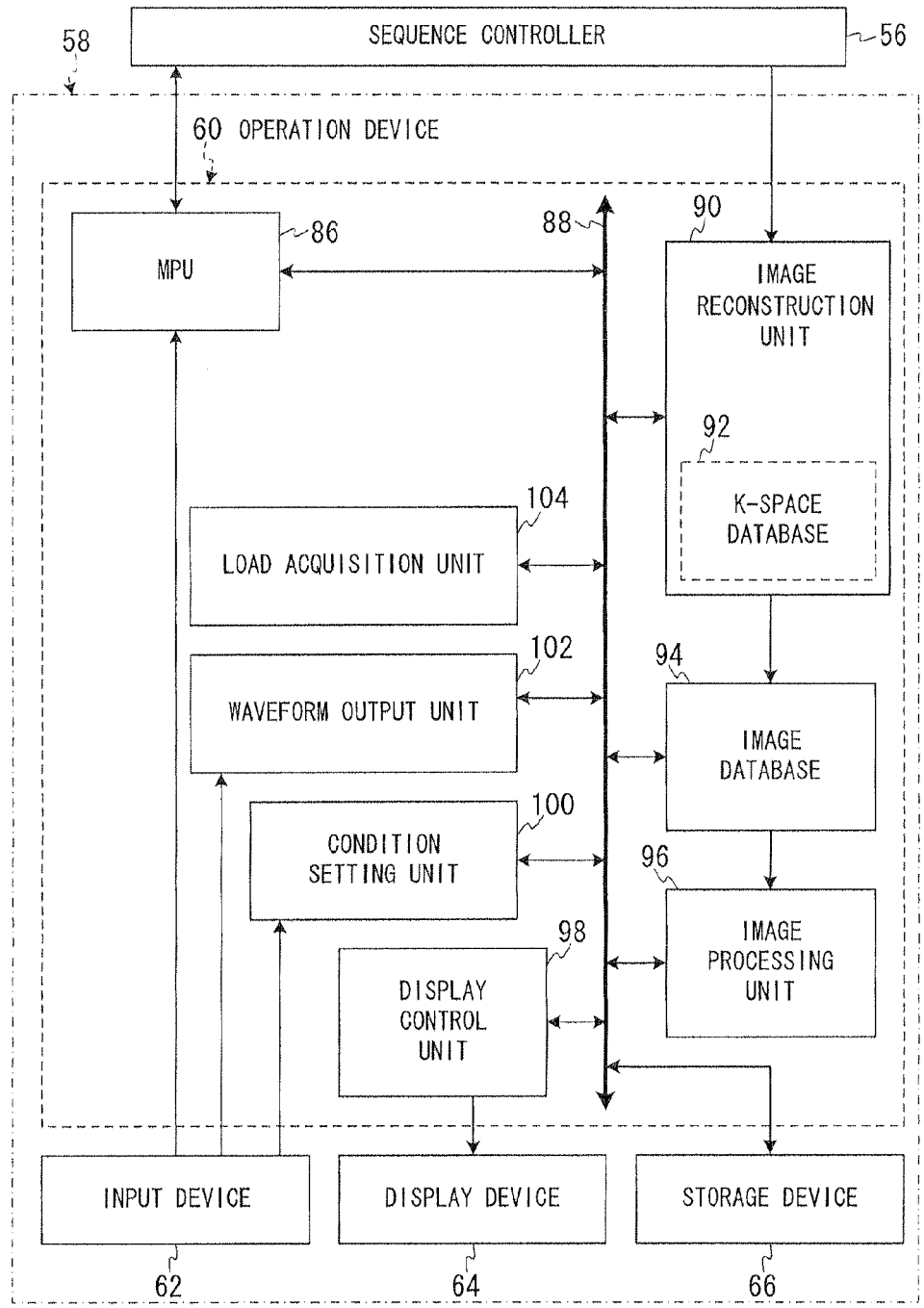
FIG. 2 is a functional block diagram of the computer 58 shown in FIG. 1.

FIG. 2 is a functional block diagram of the computer 58 shown in FIG. 1.

As shown in FIG. 2, the operation device 60 of the computer 58 includes an MPU (Micro Processor Unit) 86, a system bus 88, an image reconstruction unit 90, an image database 94, an image processing unit 96, a display controlling unit 98, a condition setting unit 100, a waveform output unit 102 and a load acquisition unit 104.

The MPU 86 performs system control of the MRI apparatus 20 in setting of imaging conditions of a main scan, imaging operation and image display after imaging through interconnection such as the system bus 88. In order to achieve it, the MPU 86 controls the display controlling unit 98 and displays screen information for setting the imaging conditions on the display device 64.

The aforementioned imaging condition refers to under what condition an RF signal or the like is transmitted in what type of imaging sequence (pulse sequence and under what condition an MR signal is acquired from an object in a main scan, for example.

As a parameter of the "imaging conditions", for example, there are the imaging region, an application method of gradient magnetic fields, the number of slices, an imaging part, the type of the imaging sequence such as parallel imaging, and so on.

The aforementioned "imaging part" means a region of the object P to be imaged, such as a head, a chest, an abdomen, and so on.

The aforementioned "main scan" is a scan for imaging an intended diagnosis image such as a T1 weighted image, and it does not include a scan for acquiring MR signals for a scout image or a calibration scan. A scan is an operation of acquiring MR signals, and it does not include image reconstruction processing.

The calibration scan is a scan for determining unconfirmed elements of imaging conditions, conditions and data used for image reconstruction processing after the main scan and so on, and it is performed separately from the main scan. Here, as an example, a calibration scan which is performed before the main scan is referred to as a prescan. A sequence of calculating a center frequency of an RF pulse in the main scan is an example of the calibration scan.

The MPU 86 inputs the imaging sequence set by the condition setting unit 100 to the sequence controller 56.

The input device 62 provides a user with a function to set the imaging conditions and image processing conditions.

The image reconstruction unit 90 includes a k-space database 92 inside. The image reconstruction unit 90 arranges the raw data of MR signals inputted from the sequence controller 56 in the k-space formed in the k-space database 92 as k-space data. The image reconstruction unit 90 generates image data of each slice of the object P by performing image reconstruction processing including such as 2-dimensional Fourier transformation on the k-space data. The image reconstruction unit 90 stores the generated image data in the image database 94.

The image processing unit 96 takes in the image data from the image database 94, performs predetermined image processing on them, and stores the image data after the image processing in the storage device 66 as image data for display.

The storage device 66 stores the image data for display after adding accompanying information such as the imaging conditions used for generating the image data for display and information of the object P (patient information) to the image data for display.

The display controlling unit 98 displays a screen for setting the imaging conditions and an image indicated by generated image data through imaging on the display device 64 under control of the MPU 86.

The condition setting unit 100 sets the imaging conditions based on a portion of imaging conditions (inputted information) inputted to the input device 62. An imaging sequence is defined by the imaging conditions.

Additionally, the condition setting unit 100 sets the imaging conditions again so as to satisfy predetermined conditions, when the condition setting unit 100 receives a resetting command of imaging conditions (its details will be explained in the after-mentioned step S6).

The waveform output unit 102 calculates waveforms of gradient magnetic fields based on "the imaging conditions (imaging sequence defined by imaging conditions) set by the condition setting unit 100", and outputs the waveforms.

The load acquisition unit 104 separates the waveforms of gradient magnetic fields calculated by the waveform output unit 102 into a plurality of frequency bands, and calculates electric loads of respective frequency bands imposed on the gradient magnetic field generation system. The aforementioned gradient magnetic field generation system corresponds to, for example, the gradient magnetic field power supply 44, the gradient magnetic field coil 26, cables which electrically connects them each other (the bold line part in FIG. 1) and the EMC filters 45x, 45y, 45z inserted in these cables, in FIG. 1.

The load acquisition unit 104 judges (determines) whether the set imaging sequence is practicable or not, based on the electric loads. Then, the load acquisition unit 104 inputs a resetting command of imaging conditions to the condition setting unit 100, if the judgment result is negative (impracticable).

Here, the inventor of the present invention focused attention on the following point. That is, impedance of the gradient magnetic field coil 26 changes depending on the frequency of electric current supplied to the gradient magnetic field coil 26. For example, in some cases, the impedance increases depending on increase in frequency.

Then, the inventor of the present invention has worked out an extremely groundbreaking method in which frequency separation is performed so as to calculate the electric loads of respective frequency bands and then these electric loads are summed up to accurately calculate the total electric load on the gradient magnetic field generation system. Hereinafter, this method will be explained in detail step by step.

Figure 3:
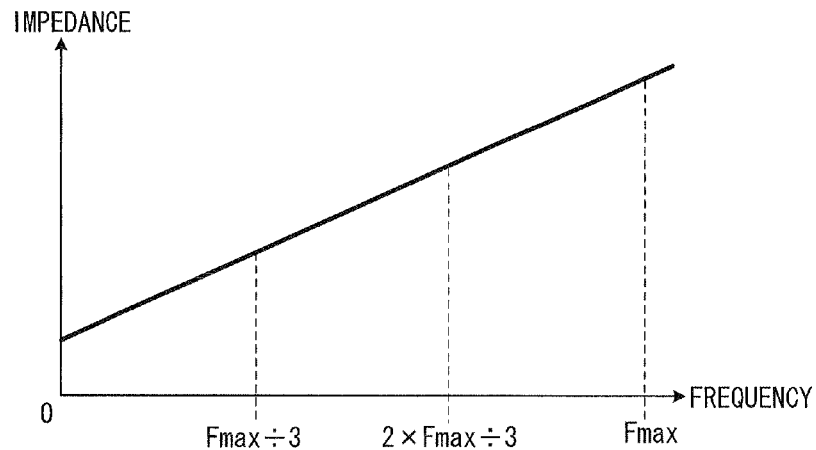
FIG. 3 is a schematic diagram showing an example of frequency separation, when impedance of a gradient magnetic field coil increases as a linear function in accordance with frequency increase in electric current supplied to the gradient magnetic field coil.
Figure 4:
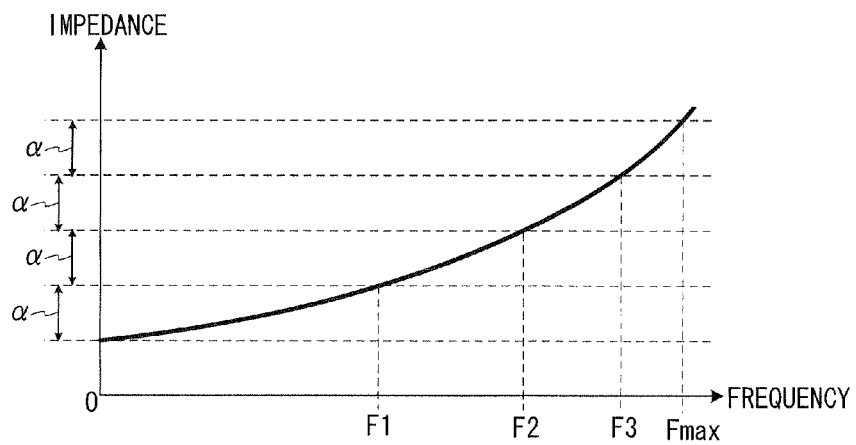
FIG. 4 is a schematic diagram showing an example of frequency separation, when the higher the frequency of electric current supplied to the gradient magnetic field coil is, the larger the increased amount in impedance per increased unit frequency becomes.

FIG. 3 and FIG. 4 are explanatory diagrams, each of which shows an example of separating waveforms of gradient magnetic fields into a plurality of frequency band. FIG. 3 and FIG. 4 correspond to a case where the impedance of the gradient magnetic field coil 26 increases as the electric current supplied to the gradient magnetic field coil 26 increases.

FIG. 3 is a schematic diagram showing an example of the frequency separation, when the impedance of the gradient magnetic field coil 26 increases as a linear function in accordance with frequency increase in electric current supplied to the gradient magnetic field coil 26. Here, as an example, based on the maximum frequency Fmax of the electric current supplied to the gradient magnetic field coil 26, the maximum frequency Fmax is trisected into the low frequency band, the middle frequency band and the high frequency band. In FIG. 3, the low frequency band is the range from 0 to (Fmax/3) hertz, the middle frequency band is the range from (Fmax/3) to (2×Fmax/3) hertz, and the high frequency band is the range from (2×Fmax/3) to Fmax hertz.

Note that, the larger the separation number is, the more precisely the electric load on the gradient magnetic field generation system can be calculated. However, the larger the separation number is, the more time and memory capacity are required for the calculation processing. Therefore, the separation number is not limited to the aforementioned three but is satisfactory if it is plural. It is desirable to determine the separation number so that the time and memory capacity required for the calculation become acceptable degree as a part of the entire operation of the MRI apparatus 20.

FIG. 4 is a schematic diagram showing an example of the frequency separation, when the higher the frequency is, the larger the increased amount in impedance per increased unit frequency becomes. Here, as an example, the frequency separation is performed in such a manner that the difference between the maximum impedance and the minimum impedance in every separated frequency band is mutually equal to a predetermined value ($\alpha$ in FIG. 3).

In the example of FIG. 4, the first frequency band is the range from 0 to F1 hertz, the second frequency band is the range from F1 to F2 hertz, the third frequency band is the range from F2 to F3 hertz, and the fourth frequency band is the range from F3 to Fmax hertz.

As just described, the load acquisition unit 104 separates the waveforms of the gradient magnetic fields into a plurality of frequency bands depending on the frequency characteristics of the impedance of the gradient magnetic field coil 26.

Additionally, the X axis gradient magnetic field coil 26x, the Y axis gradient magnetic field coil 26y and the Z axis gradient magnetic field coil 26z do not accord with each other in terms of the frequency characteristics of impedance, because they are different from each other in curling configuration and so on.

Then, the load acquisition unit 104 changes each range of each frequency band for the X axis, the Y axis and the Z axis gradient magnetic field coil 26x, 26y, 26z, keeping each separation number the same.

In particular, for example, when the low frequency band is 0 to 200 hertz, the middle frequency band is 200 to 600 hertz and the high frequency band is 600 to Fmax hertz for the X axis gradient magnetic field coil 26x, each frequency band of the Y axis gradient magnetic field coil 26y is changed as follows. That is, the low frequency band is 0 to 250 hertz, the middle frequency band is 250 to 700 hertz and the high frequency band is 700 to Fmax hertz, for the Y axis gradient magnetic field coil 26y.

Here, as a calculation method of the electric load on the gradient magnetic field generation system, a case of diffusion weighted imaging in which an MPG pulse is applied in a pulse sequence of single shot EPI of spin echo system will be explained. Note that, the aforementioned EPI means echo planar imaging, the aforementioned MPG pulse means a diffusion gradient magnetic field (motion probing gradient).

Figure 5:
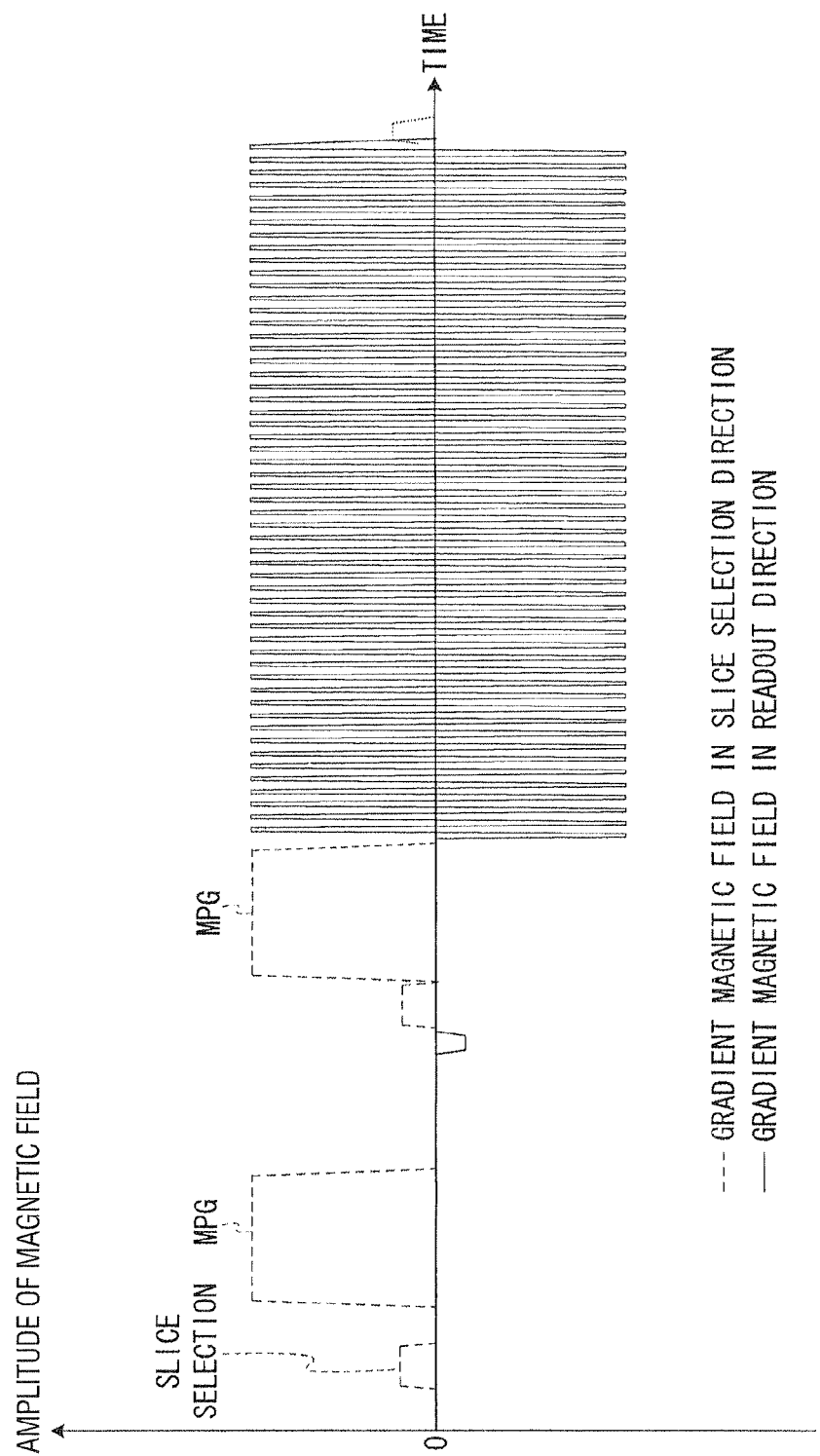
FIG. 5 is a schematic diagram showing an example of waveforms of respective gradient magnetic fields in a slice selection direction and a readout direction in a pulse sequence of single shot EPI of spin echo system.
Figure 6:
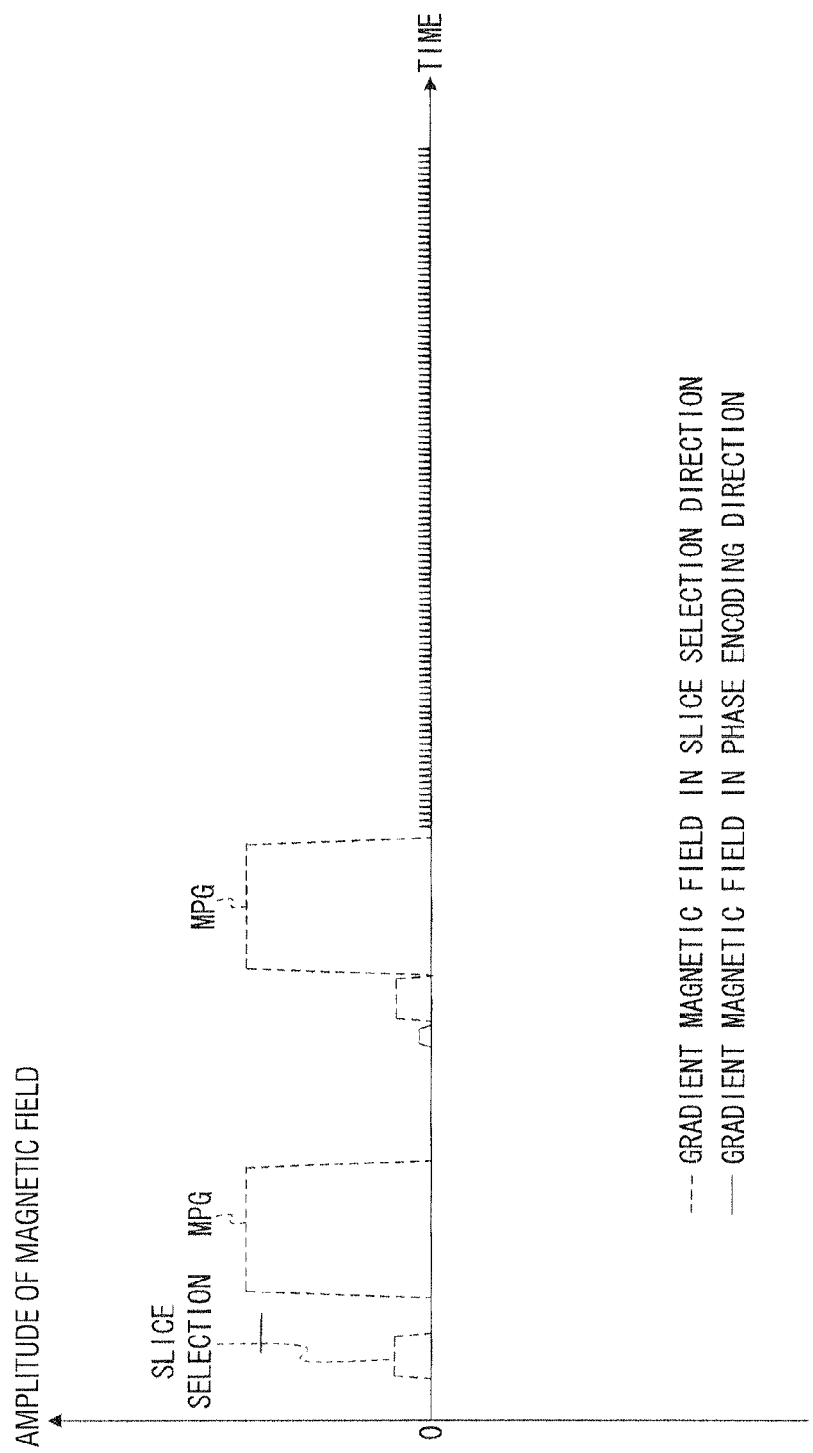
FIG. 6 is a schematic diagram showing an example of waveforms of the respective gradient magnetic fields in the slice selection direction and a phase encode direction in the pulse sequence of single shot EPI of spin echo system.

FIG. 5 and FIG. 6 are schematic diagrams showing examples of waveforms of respective gradient magnetic fields in a pulse sequence of the single shot EPI of spin echo system. Because it is cumbersome in the case of showing three directions in one chart in one lump, the waveforms of the gradient magnetic field in the slice selection direction Gss and the gradient magnetic field in the readout direction Gro are shown in FIG. 5. In FIG. 6, the waveforms of the gradient magnetic field in the slice selection direction Gss and the gradient magnetic field in the phase encode direction Gpe are shown.

In FIG. 5 and FIG. 6, the abscissa axis indicates elapsed time, and the vertical axis indicates amplitude of the gradient magnetic field, respectively. Additionally, in FIG. 5 and FIG. 6, the gradient magnetic field in the slice selection direction Gss is commonly shown as dash lines, the gradient magnetic field in the readout direction Gro (only in FIG. 5) is shown as a solid line, the gradient magnetic field in the phase encode direction Gpe (only in FIG. 6) is shown as a solid line. The aforementioned signage applies to the after-mentioned FIG. 7 to FIG. 12.

Note that, for simplicity of explanation, it is assumed that each of the three axes of the apparatus coordinate system accord with one of the slice selection direction, the phase encode direction and the readout direction. That is, each of the X axis, the Y axis and the Z axis gradient magnetic field coils 26x, 26y, 26z forms one of the gradient magnetic field in the slice selection direction. Gss, the gradient magnetic field in the phase encode direction Gpe and the gradient magnetic field in the readout direction Gro. Thus, the vertical axis is strength of one of the X axis gradient magnetic field Gx, the Y axis gradient magnetic field Gy and the Z axis gradient magnetic field Gz. That is, the vertical axis approximately corresponds to an electric current value supplied to one of the X axis gradient magnetic field coil 26x, the Y axis gradient magnetic field coil 26y and Z axis gradient magnetic field coil 26z.

Note that, the present embodiment is not limited to the aforementioned aspect. The present embodiment is applicable to imaging of a slice slanting from the X-Y plane, the Y-Z plane or the X-Z plane of the apparatus coordinate system.

That is, the X axis, the Y axis and the Z axis gradient magnetic field Gx, Gy, Gz may be calculated in the way similar to the aforementioned manner based on a pulse sequence in which the gradient magnetic field in the slice selection direction Gss, the gradient magnetic field in the phase encode direction Gpe and the gradient magnetic field in the readout direction Gro are prescribed. Thereby, each electric current value supplied to each of the X axis gradient magnetic field coil 26x, the Y axis gradient magnetic field coil 26y and Z axis gradient magnetic field coil 26z can be calculated, and then the electric load on the gradient magnetic field generation system can be calculated similarly.

Hereinafter, the pulse sequence in FIG. 5 and FIG. 6 will be briefly explained. First, under application of the gradient magnetic field in the slice selection direction Gss, an intended slice is excited by transmitting a 90° RF pulse from the RF coil 28 to the imaging region. Next, the first MPG pulse is applied in the readout direction.

Next, in order to generate an echo signal by inverting magnetization of the excited region, a gradient magnetic field is applied in the slice selection direction, and a 180° RF pulse for refocusing is transmitted from the RF coil 28 to the imaging region.

Next, the second MPG pulse is applied in the readout direction. After this, gradient magnetic fields are applied in the readout direction by reversing polarity thereof, while gradient magnetic field pulses are applied in the phase encode direction at specified time intervals. Thereby, MR signals (echo signals) for image reconstruction are acquired.

FIG. 7 to FIG. 12 are schematic diagrams each showing an example of the waveforms of respective gradient magnetic fields, when the frequency separation is performed on the pulse sequence in FIG. 5 and FIG. 6 in the manner shown in FIG. 3.

Figure 7:
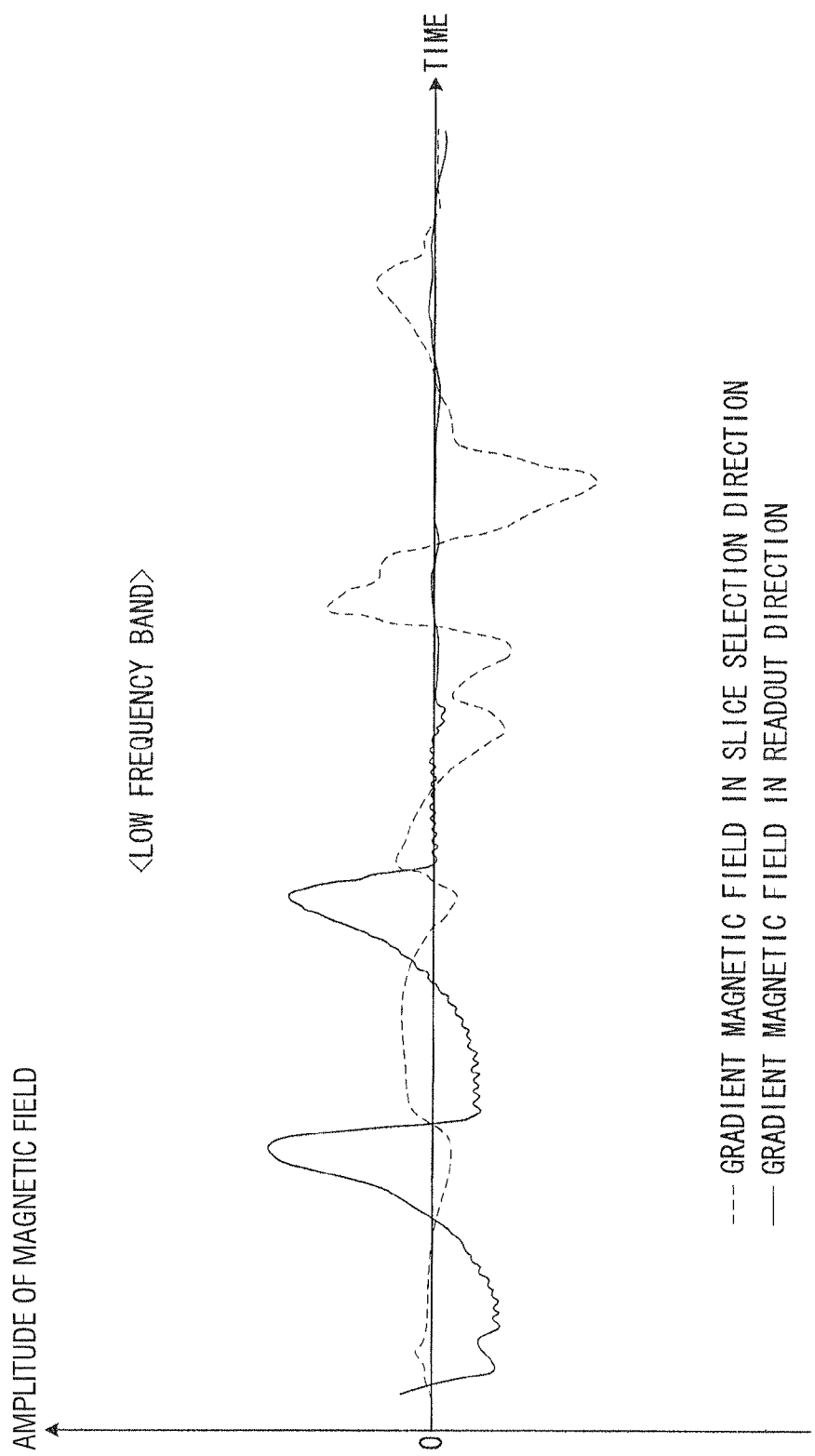
FIG. 7 is a schematic diagram showing an example of waveforms of the respective gradient magnetic fields in the slice selection direction and the phase encode direction in a low frequency band, when frequency separation is performed on the pulse sequence in FIG. 5 and FIG. 6 in the manner shown in FIG. 3.
Figure 8:
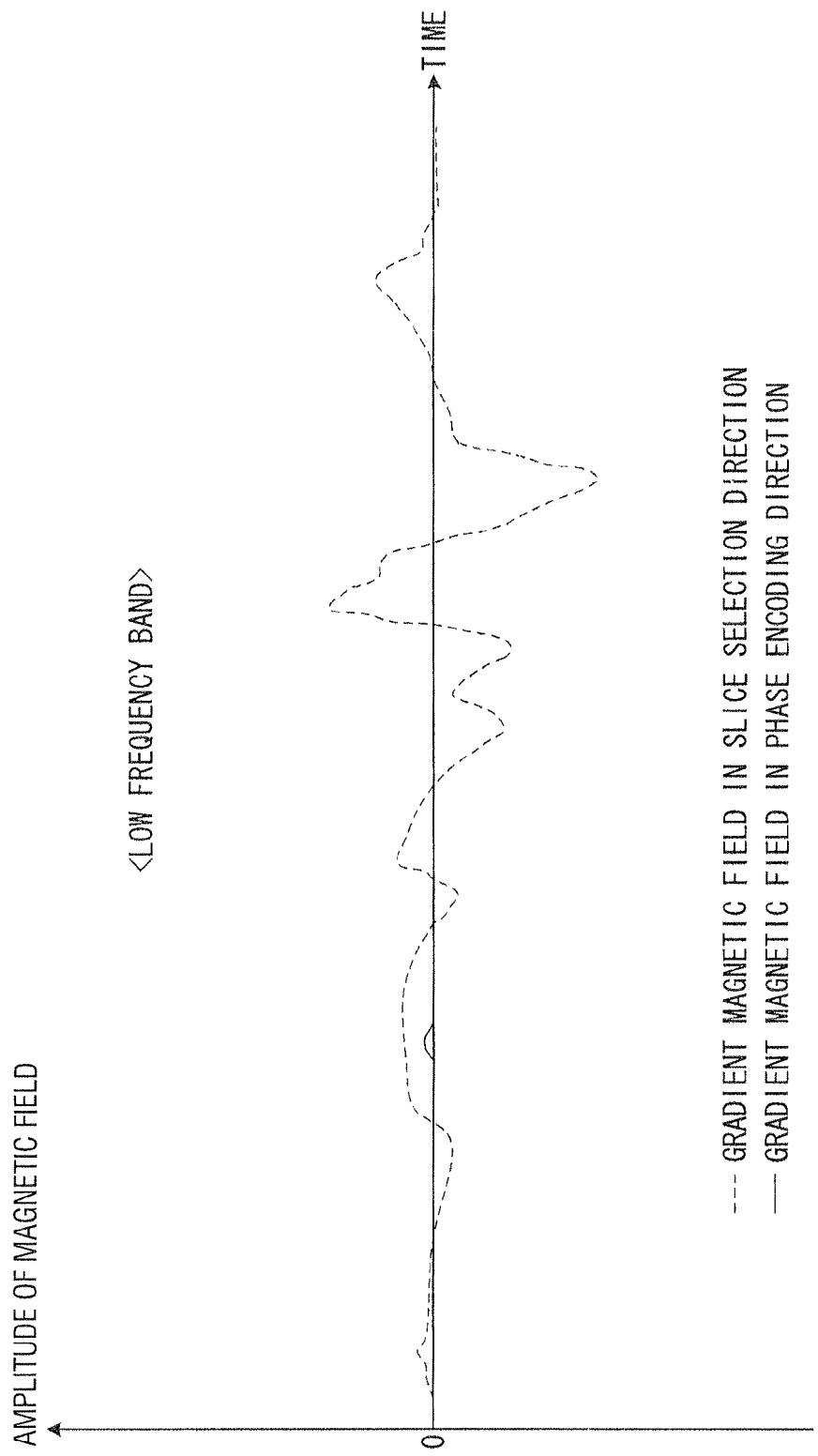
FIG. 8 is a schematic diagram showing an example of waveforms of the respective gradient magnetic fields in the slice selection direction and the phase encode direction in the low frequency band, when frequency separation is performed on the pulse sequence in FIG. 5 and FIG. 6 in the manner shown in FIG. 3.

FIG. 7 and FIG. 8 indicate the gradient magnetic field waveforms in the aforementioned low frequency band.

Figure 9:
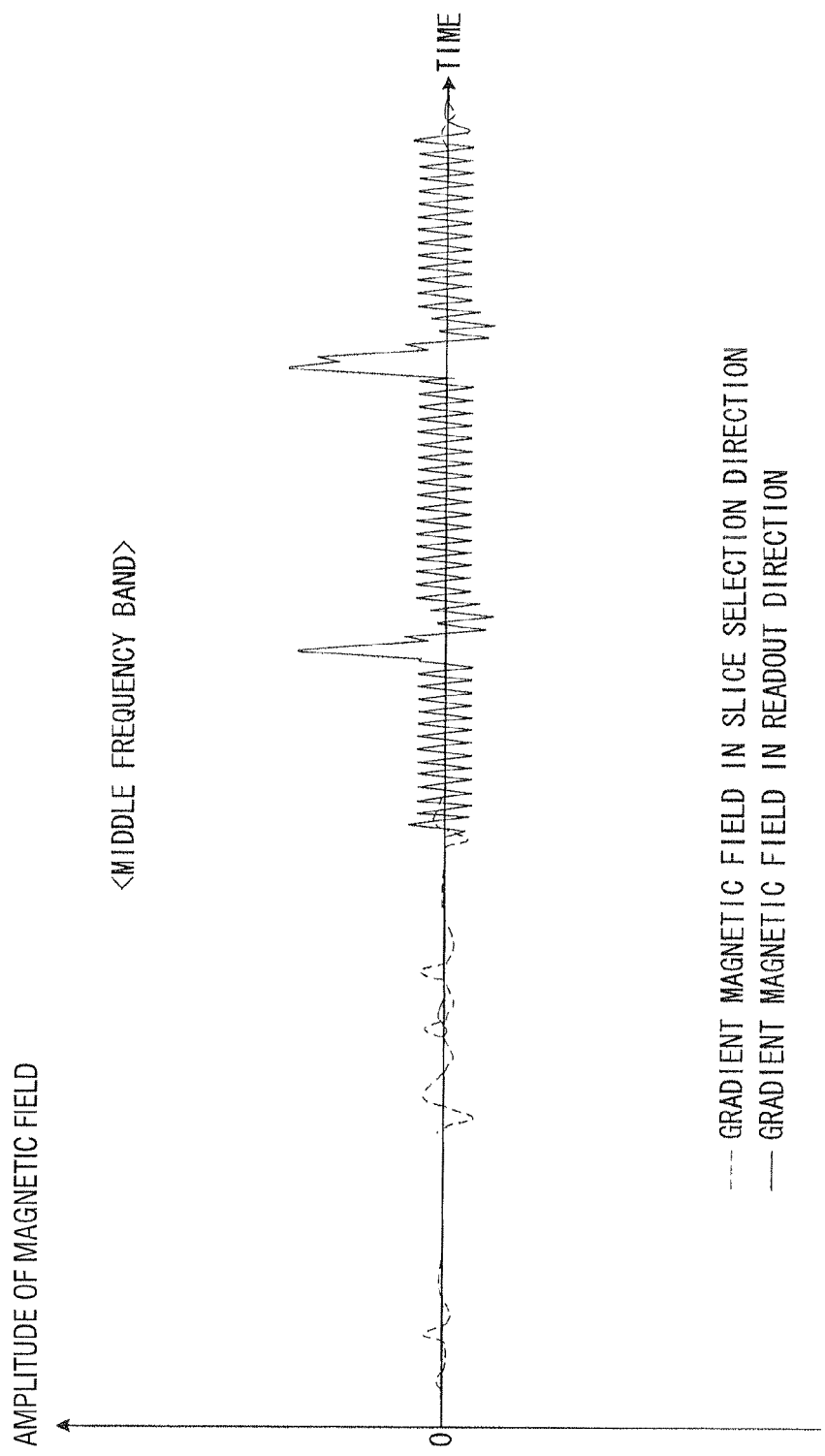
FIG. 9 is a schematic diagram showing an example of waveforms of the respective gradient magnetic fields in the slice selection direction and the readout direction in a middle frequency band, when frequency separation is performed on the pulse sequence in FIG. 5 and FIG. 6 in the manner shown in FIG. 3.
Figure 10:
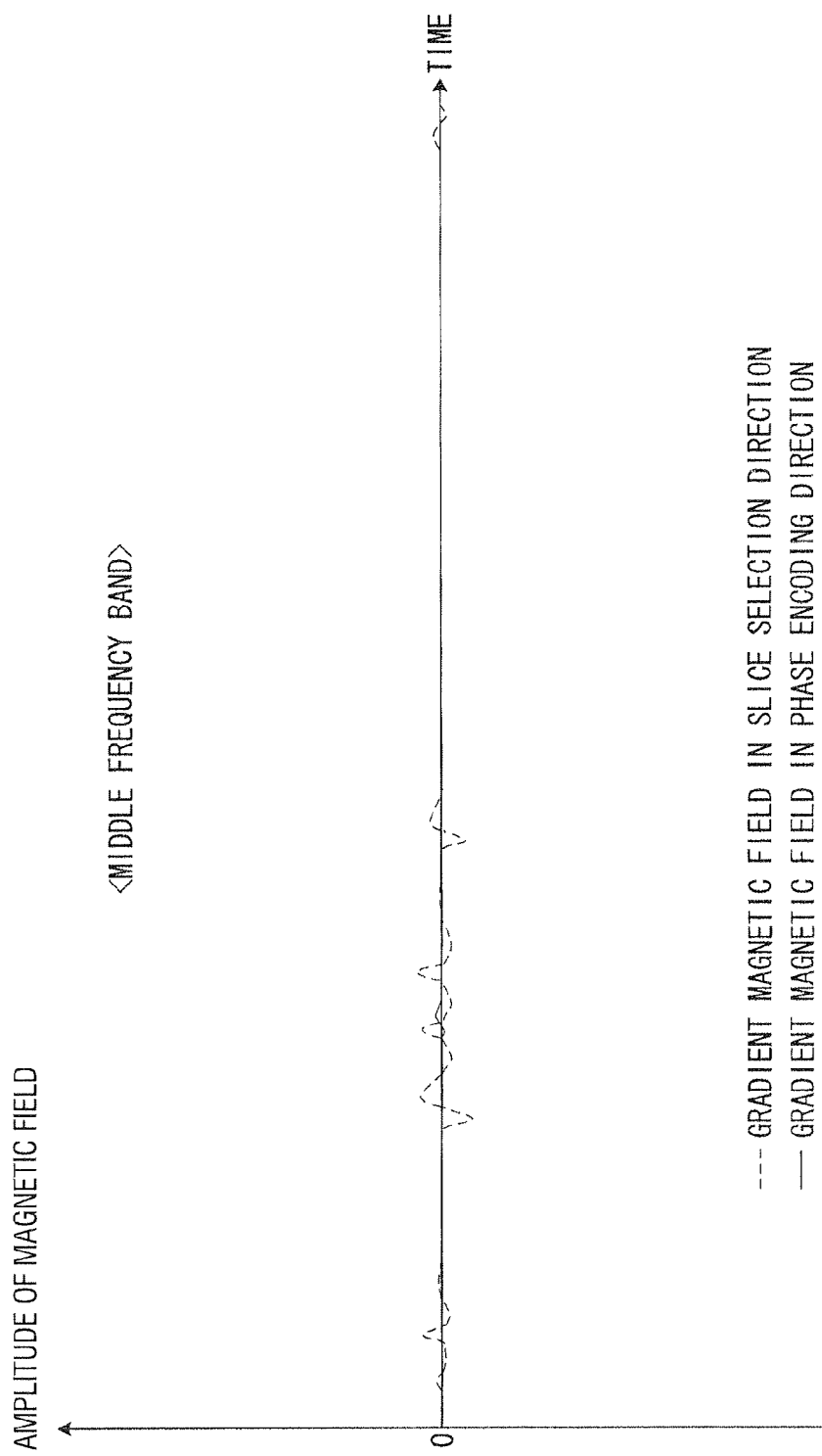
FIG. 10 is a schematic diagram showing an example of waveforms of the respective gradient magnetic fields in the slice selection direction and the phase encode direction in the middle frequency band, when frequency separation is performed on the pulse sequence in FIG. 5 and FIG. 6 in the manner shown in FIG. 3.

FIG. 9 and FIG. 10 indicate the gradient magnetic field waveforms in the aforementioned middle frequency band.

Figure 11:
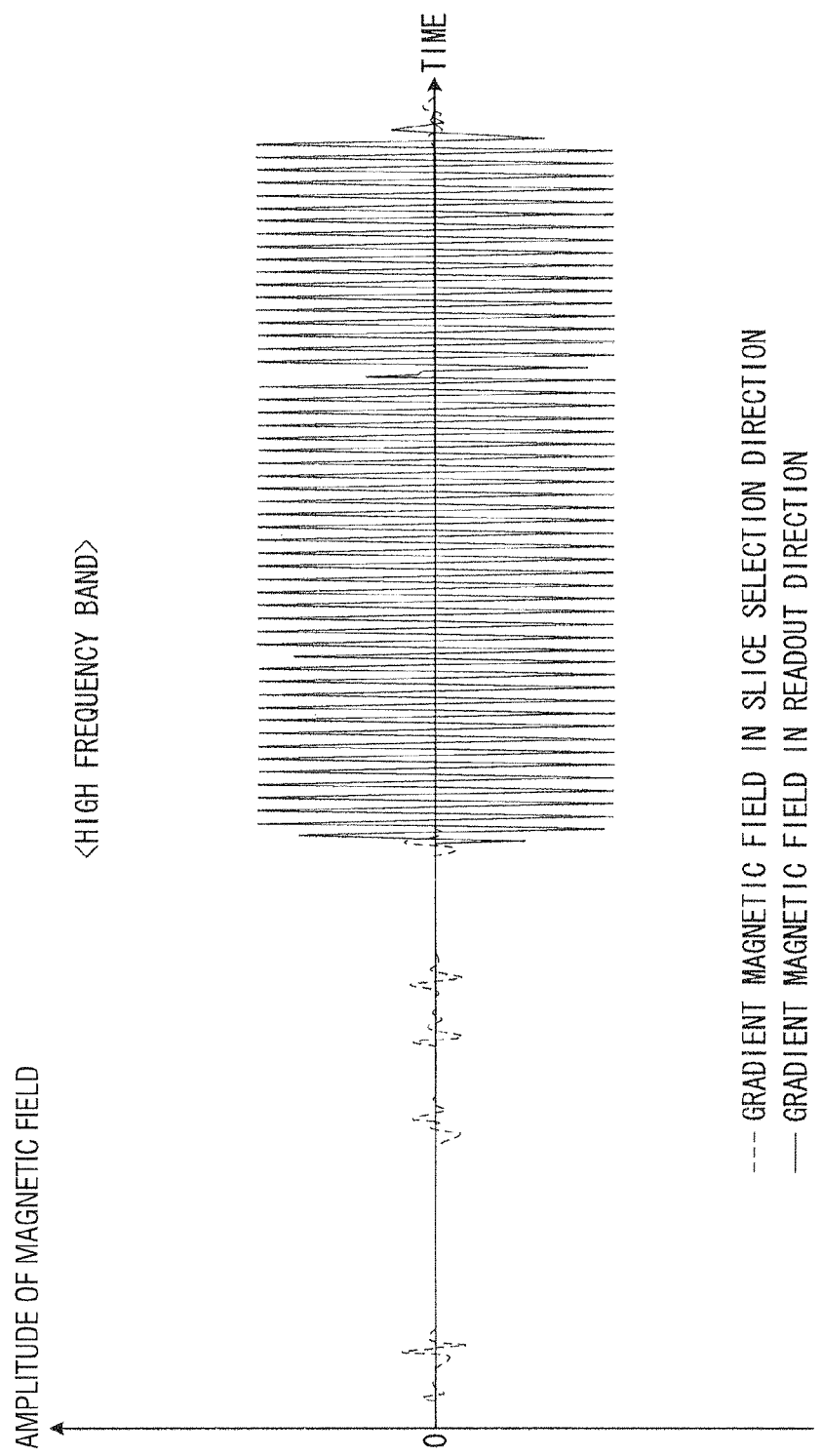
FIG. 11 is a schematic diagram showing an example of waveforms of the respective gradient magnetic fields in the slice selection direction and the readout direction in a high frequency band, when frequency separation is performed on the pulse sequence in FIG. 5 and FIG. 6 in the manner shown in FIG. 3.
Figure 12:
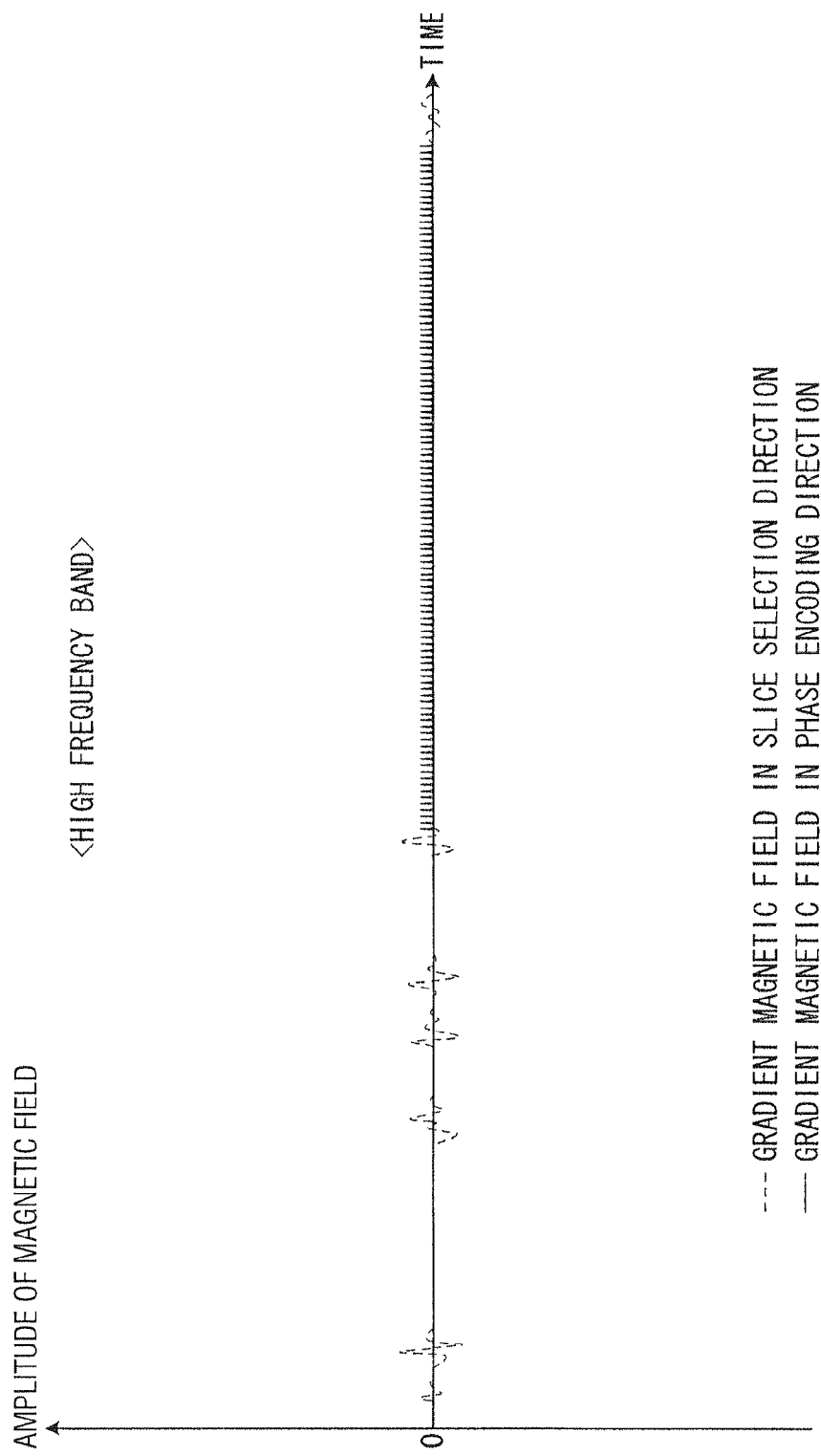
FIG. 12 is a schematic diagram showing an example of waveforms of the respective gradient magnetic fields in the slice selection direction and the phase encode direction in the high frequency band, when frequency separation is performed on the pulse sequence in FIG. 5 and FIG. 6 in the manner shown in FIG. 3.

FIG. 11 and FIG. 12 indicate the gradient magnetic field waveforms in the aforementioned high frequency band.

Additionally, because it is cumbersome in the case of showing the gradient magnetic field waveforms of three directions in one figure in one lump, FIG. 7, FIG. 9 and FIG. 11 indicate waveforms of the gradient magnetic field in the slice selection direction Gss and the gradient magnetic field in the readout direction Gro. In FIG. 8, FIG. 10 and FIG. 12, waveforms of the gradient magnetic field in the slice selection direction Gss and the gradient magnetic field in the phase encode direction Gpe are shown.

In order to separate the gradient magnetic field waveforms of the pulse sequence shown in FIG. 5 and FIG. 6 into the gradient magnetic field waveforms of respective frequency bands as shown in FIG. 7 to FIG. 12, for example, a digital filter which makes only intended frequency band of the original gradient magnetic field waveforms selectively pass may be applied.

As an architecting method of such a filter which makes only intended frequency band selectively pass, for example, there are following methods. That is, appropriate filters are selected out of IIR (Infinite Impulse Response) filters such as a Chebyshev filter, a Butterworth filter and FIR (Finite Impulse Response) filters, and then conditions such as tap number (number of filter coefficients) may be appropriately set. The load acquisition unit 104 includes many sorts of the aforementioned filters for frequency separation.

Here, the vertical axis of the gradient magnetic field waveforms separated per frequency band corresponds to amplitude of electric current supplied to the gradient magnetic field coil as mentioned before, and its sign become plus and minus. Therefore, if the electric load is calculated by uniting the sign so as to become intensity, the calculation becomes less complicated.

Then, in the present embodiment, as to the gradient magnetic field waveforms (in FIG. 7 to FIG. 12) separated per frequency band, the abscissa axis (elapsed time) is kept unchanged while values of the vertical axis are squared. After such transformation, values of the vertical axis correspond to square of electric current (power/resistance value), parts whose sign are minus are all reversed to become positive values. Therefore, the electric load corresponding to the power can be calculated by multiplying these transformed values of the vertical axis by the value corresponding to the resistance value.

More specifically, a time integral value whose integral interval is from a starting time to a finish time of an imaging sequence is calculated for the transformed values of the vertical axis which corresponds to square of electric current.

This time integral value is normalized in the following manner. That is, this time integral value is divided by a time integral value of full output (in the case of supplying the maximum electric current from the starting time to the finish time). Then, the result of this division process is referred to as the power duty, hereinafter.

The power duty becomes equal to or larger than 0, and is equal to or smaller than 3. The electric load of one channel (one of the X axis, the Y axis and the Z axis) of one frequency band can be calculated by multiplying the power duty by "the load coefficient which corresponds to impedance". The aforementioned load coefficient is different depending on each channel of the X axis, the Y axis and the Z axis. The load coefficient is different depending on a frequency band. The determination method of the load coefficient will be discussed later.

The electric load of the entire X channel (hereinafter referred to as the X channel electric load Lx) can be calculated by summing up the electric loads of the X channel in all the separated frequency bands. The Y channel electric load Ly and the Z channel electric load Lz are calculated by applying the similar calculation to the Y channel and the Y channel, respectively. The total electric load Lt imposed on the gradient magnetic field generation system can be calculated by summing up the X channel electric load Lx, the Y channel electric load Ly and the Z channel electric load Lz. When the waveform is separated into three frequency band like in FIG. 3, the total electric load Lt can be calculated, for example, by the following equation (1).

$$\begin{aligned} Lt &= Lx + Ly + Lz \\ &= (PLx \times RLx + PMx \times RMx + PHx \times RHx) + \\ &\quad (PLy \times RLy + PMy \times RMy + PHy \times RHy) + \\ &\quad (PLz \times RLz + PMz \times RMz + PHz \times RHz) \end{aligned} \quad (1)$$

In the equation (1) consisting of three terms, the first term corresponds to the X channel electric load Lx, the second term corresponds to the Y channel electric load Ly, and the third term corresponds to the Z channel electric load Lz.

In the first term of the equation (1), PLx corresponds to the low frequency band, PMx corresponds to the middle frequency band, PHx corresponds to the high frequency band, and each of them is the power duty of the X channel.

Additionally, RLx corresponds to the low frequency band, RMx corresponds to the middle frequency band, RHx corresponds to the high frequency band, and each of them is the load coefficient of the X channel.

In the second term of the equation (1), PLy corresponds to the low frequency band, PMy corresponds to the middle frequency band, PHy corresponds to the high frequency band, and each of them is the power duty of the Y channel.

Additionally, RLy corresponds to the low frequency band, RMy corresponds to the middle frequency band, RHy corresponds to the high frequency band, and each of them is the load coefficient of the Y channel.

In the third term of the equation (1), PLz corresponds to the low frequency band, PMz corresponds to the middle frequency band, PHz corresponds to the high frequency band, and each of them is the power duty of the Z channel.

Additionally, RLz corresponds to the low frequency band, RMz corresponds to the middle frequency band, RHz corresponds to the high frequency band, and each of them is the load coefficient of the Z channel.

Because each power duty is normalized and is an absolute number, each load coefficient may be an absolute number. In this case, the total electric load Lt becomes an absolute number. Additionally, the range of the low frequency band is different depending on each of the X channel, the Y channel and the Z channel, as previously explained. It is the same as the middle frequency band and the high frequency band.

Note that, the present embodiment is not limited to calculation based on absolute numbers. For example, each power duty may be converted into a unit of (square of ampere)×time, each load coefficient may be converted into a unit of impedance, and then the total electric load Lt may be calculated in terms of watt×time.

Here, each load coefficient can be calculated by simulation based on specifications of the gradient magnetic field power supply 44 and so on, after measuring frequency characteristics of each impedance of the X axis, the Y axis and the Z axis gradient magnetic field coils 26x, 26y, 26z, for example.

In the simulation, the gradient magnetic field waveforms of an actual pulse sequence are outputted, frequency separation is performed on these waveforms per channel, and then each load coefficient is calculated. In this calculation of each electric load, each load coefficient may be determined so as to accord with frequency characteristics of each impedance of the X axis, the Y axis and the Z axis gradient magnetic field coils 26x, 26y, 26z.

Additionally, it is preferable to measure the voltage difference between the plus side input terminal and the minus side input terminal of the gradient magnetic field power supply 44 and time variation of electric current flowing the gradient magnetic field coil 26 under actual performance of a pulse sequence, calculate each electric load based on this measurement, and check whether or not each electric load calculated by the measured values accord with each load coefficient calculated by the simulation. If there is a slight gap in the result of the above check, each load coefficient may be corrected based on the measured values.

Here, in the measurement of checking each load coefficient, every unit of the MRI apparatus 20 is appropriately connected with each other. Therefore, each electric load is calculated as a value of the load imposed on the entire gradient magnetic field generation system including the gradient magnetic field power supply 44, the gradient magnetic field coil 26, cables connecting them each other and the EMC filters 45x, 45y, 45z. Thus, the value of each load coefficient becomes a value which reflects the entire gradient magnetic field generation system.

Then, one set of the load coefficients (hereinafter referred to as the load coefficients group) calculated per frequency band corresponding to one frequency separation method is preliminarily stored in the load acquisition unit 104 as table data. Similar simulations are performed by changing the frequency separation method, and the aforementioned load coefficients group is calculated again and stored in the load acquisition unit 104. Similarly, the frequency separation methods are variously changed and the load coefficients groups which respectively correspond to the various frequency separation methods are respectively stored in the load acquisition unit 104.

The load acquisition unit 104 preliminarily stores the load coefficients groups and the frequency characteristic of impedance of the X axis, the Y axis and the Z axis gradient magnetic field coils 26x, 26y, 26z which respectively correspond to the various frequency separation methods as just described. Thereby, even if the frequency separation method is changed according to a set pulse sequence, the electric loads can be calculated.

Note that, the gradient magnetic field generation system is not capable of continuing to supply the maximum electric current in all the channels (each gradient magnetic field coil in the X axis direction, the Y axis direction and the Z axis direction) simultaneously. There are various restrictions such as the upper limit of the entire electric power, the upper limit of each channel and so on. Therefore, the load acquisition unit 104 stores the maximum electric load Lmax which is admissible (acceptable) for the gradient magnetic field generation system. The maximum electric load Lmax can be calculated by simulation based on specification of respective units such as the X axis, the Y axis and the Z axis gradient magnetic field coils 26x, 26y, 26z and the gradient magnetic field power supply 44.

Similarly, the total electric load Lt can be calculated, for example, by the following equation (2), when the waveforms are separated into four frequency bands like in FIG. 4.

$$\begin{aligned} Lt &= Lx + Ly + Lz \\ &= (P1x \times R1x + P2x \times R2x + P3x \times R3x + P4x \times R4x) + \\ &\quad (P1y \times R1y + P2y \times R2y + P3y \times R3y + P4y \times R4y) + \\ &\quad (P1z \times R1z + P2z \times R2z + P3z \times R3z + P4z \times R4z) \end{aligned} \quad (2)$$

In the equation (2), the first term is the X channel electric load Lx, the second term is the Y channel electric load Ly, and the third term is the Z channel electric load Lz.

In the first term of the equation (2), P1x corresponds to the first frequency band, P2x corresponds to the second frequency band, P3x corresponds to the third frequency band, P4x corresponds to the fourth frequency band, and each of these four is the power duty of the X channel. Additionally, R1x corresponds to the first frequency band, R2x corresponds to the second frequency band, R3x corresponds to the third frequency band, R4x corresponds to the fourth frequency band, and each of these four is the load coefficient of the X channel. The second and third terms of the equation (2) are similar to the aforementioned first term.

The load acquisition unit 104 judges (determines) whether or not the total electric load Lt is larger than "the maximum electric load Lmax which is an allowable amount of power supply for the gradient magnetic field generation system". If the total electric load Lt is larger than the maximum electric load Lmax, the load acquisition unit 104 judges that the currently set imaging sequence is impracticable. Hereinafter, three examples of FIG. 13, FIG. 14 and FIG. 15 will be explained as processing when an imaging sequence is judged impracticable.

Figure 13:
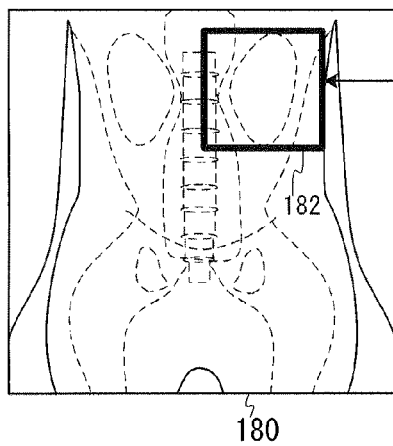
FIG. 13 is a schematic diagram showing an example of display of a caution notice in a viewing surface for setting imaging conditions.

FIG. 13 is a schematic diagram showing an example of display of a caution notice in a viewing surface for setting imaging conditions. In the example of FIG. 13, a bold-line frame 182 of FOV (Field Of View) is displayed inside a scout image 180, and boxes 184, 190, 192, 194 and 196 for setting imaging conditions are displayed on the right side of the scout image 180.

The display of the box 184 indicates that FOV is currently set to 125 mm×125 mm.

The display of the box 190 indicates that the slice number is currently set to 100.

The display of the box 192 indicates that the repetition time TR is currently set to 500 ms.

The display of the box 194 indicates that the phase encode step number is currently set to 256.

The display of the box 196 indicates that the frequency encode step number is currently set to 256.

Here, as an example, the load acquisition unit 104 makes the display device 64 display a caution notice indicating that the imaging sequence (stipulated by the currently set imaging conditions) is impracticable at the top of the screen as textual information by controlling the display control unit 98. A user can change imaging conditions by altering (changing) each value of each parameter, manipulating the input device 62.

That is, a user can change (reset) imaging conditions so as to reduce the electric load by alteration of a condition such as decreasing the slice number and so on. In this case, the total electric load Lt is calculated based on the updated imaging conditions, and "the judgment as to whether the total electric load Lt is equal to or less than the maximum electric load Lmax or not" is performed again.

Figure 14:
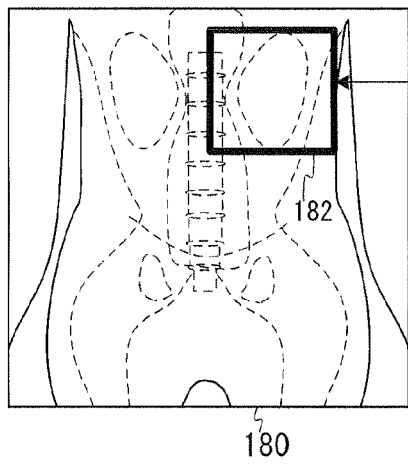
FIG. 14 is a schematic diagram showing an example of display of correction options of imaging conditions, when an imaging sequence is judged impracticable.

FIG. 14 is a schematic diagram showing an example of display of correction options of imaging conditions, when an imaging sequence is judged impracticable. When an imaging sequence is judged impracticable, the condition setting unit 100 calculates a plurality of correction options of imaging conditions in such a manner that the total electric load Lt does not excess the maximum electric load Lmax.

More specifically, for example, the condition setting unit 100 calculates how much percentage the inputted total electric load Lt excesses the maximum electric load Lmax, assuming that the maximum electric load Lmax is 100%. The condition setting unit 100 calculates a plurality of correction options of imaging conditions according to the calculated excess amount so as to decrease the electric load. Concretely speaking, the electric load becomes smaller by decreasing the slice number, lengthening the repetition time TR, decreasing the application amount of MPG (b-factor), expanding FOV and so on.

Note that, if FOV is expanded, the slope of the gradient magnetic field becomes gentler and the electric load becomes smaller. This is because "a predetermined value or a value higher than the predetermined value as a difference in magnetic field intensity between one end and the opposite end of FOV" is necessary for adding positional information.

The condition setting unit 100 makes the display device 64 displays a plurality of calculated correction options of imaging conditions, by inputting them to the display control unit 98.

In the example of FIG. 14, it is displayed in the box 184 as one of the correction options of imaging conditions to expand FOV from 125 mm×125 mm to 250 mm×250 mm.

Additionally, it is displayed in the box 190 as one of the correction options of imaging conditions to decrease the slice number from 100 to 50.

Additionally, it is displayed in the box 192 as one of the correction options of imaging conditions to lengthen the repetition time TR from 500 ms to 1000 ms.

Additionally, it is displayed in the box 194 and 196 as one of the correction options of imaging conditions to decrease the phase encode step number and the frequency encode step number from 256 to 128 respectively.

A user can alter (reconfigure) the imaging conditions of the imaging sequence by selecting one or a plurality of the correction options of the imaging sequence displayed on the display device 64 via the input device 62 so as to make the imaging sequence practicable.

Figure 15:
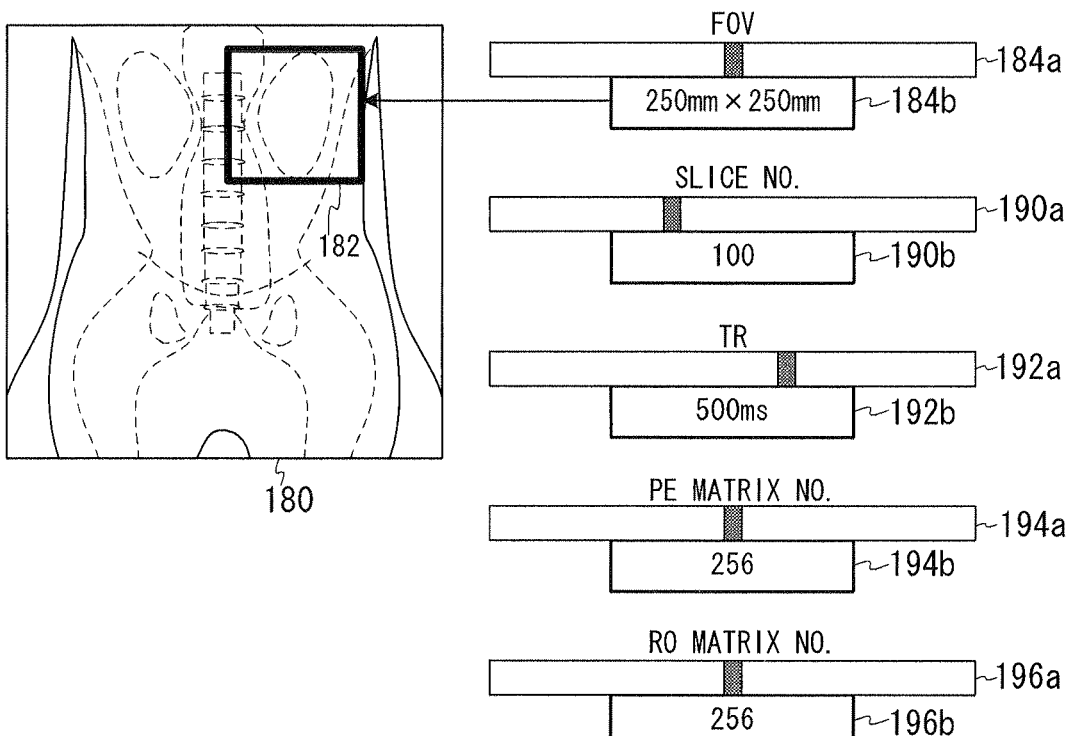
FIG. 15 is a schematic diagram showing another example of the display of correction options of imaging conditions, when an imaging sequence is judged impracticable.

FIG. 15 is a schematic diagram showing another example of display of the correction options of imaging conditions, when an imaging sequence is judged impracticable. FIG. 15 is a schematic diagram showing a screen for setting imaging conditions as a slider bar type.

In FIG. 15, a slider bar 184*a* has a function of setting FOV by moving the slider (a rectangle blackly filled in FIG. 15) inside the horizontal bar.

The box 184*b* numerically indicates the currently set FOV according to the position of the slider bar 184*a*.

Similarly, the slider bar 190*a* has a function of setting the slice number, and the box 190*b* numerically indicates the currently set slice number.

Additionally, the slider bar 192*a* has a function of setting the repetition time TR, and the box 192*b* numerically indicates the currently set repetition time TR.

Additionally, the slider bar 194*a* has a function of setting the phase encode step number, and the box 194*b* numerically indicates the currently set phase encode step number.

Additionally, the slider bar 196*a* has a function of setting the frequency encode step number, and the box 196*b* numerically indicates the currently set frequency encode step number.

When an imaging sequence is judged impracticable, for example, correction options of imaging conditions are automatically calculated in the way similar to the case explained in FIG. 14, and imaging conditions are automatically corrected.

In the example of FIG. 15, FOV is expanded (automatically set again) to the degree by which the imaging sequence becomes practicable in terms of electric power, and that effect is displayed at the top of the screen.

When a user manually alters a portion of imaging conditions so as to increase the total electric load Lt in the state of FIG. 15 (the state where imaging conditions have been automatically corrected), at least a portion of other conditions is automatically corrected in tandem with the alteration of conditions by the user. More specifically, at least one of the conditions except the condition(s) altered by the user is (are) automatically corrected in such a manner that the imaging sequence becomes practicable and the total electric load Lt changes little.

For example, assume that the repetition time is altered to one-quarter (i.e. 125 ms) by a user from the state of the FIG. 15. In this case, the condition setting unit 100 calculates respective correction options of the phase encode step number and the frequency encode step number in such a manner that the imaging sequence remains practicable and the total electric load Lt changes little.

For example, when the respective correction options are 128, the condition setting unit 100 updates (set again) the phase encode step number and the frequency encode step number to the calculated correction options respectively, and inputs these correction options to the display control unit 98.

Thereby, the display device 64 displays the updated phase encode step number and frequency encode step number in the boxes 194*b* and 196*b* respectively, and moves the sliders in the slider bars 194*a* and 196*a* to the respective positions corresponding to the respective correction options.

The aforementioned manner is only an example. When the repetition time TR is manually alerted (set again), a correction option of the slice number or FOV may be automatically calculated and the slice number or FOV may be automatically set again to the calculated correction option in tandem with the manual resetting.

Alternatively, when the repetition time TR is manually alerted (set again), the slice number, FOV, the phase encode step number, the frequency encode step number or at least one of other conditions may be automatically set again. When other conditions such as FOV are manually set again, calculation of correction option and automatic resetting of imaging conditions are performed in the same manner.

Figure 16:
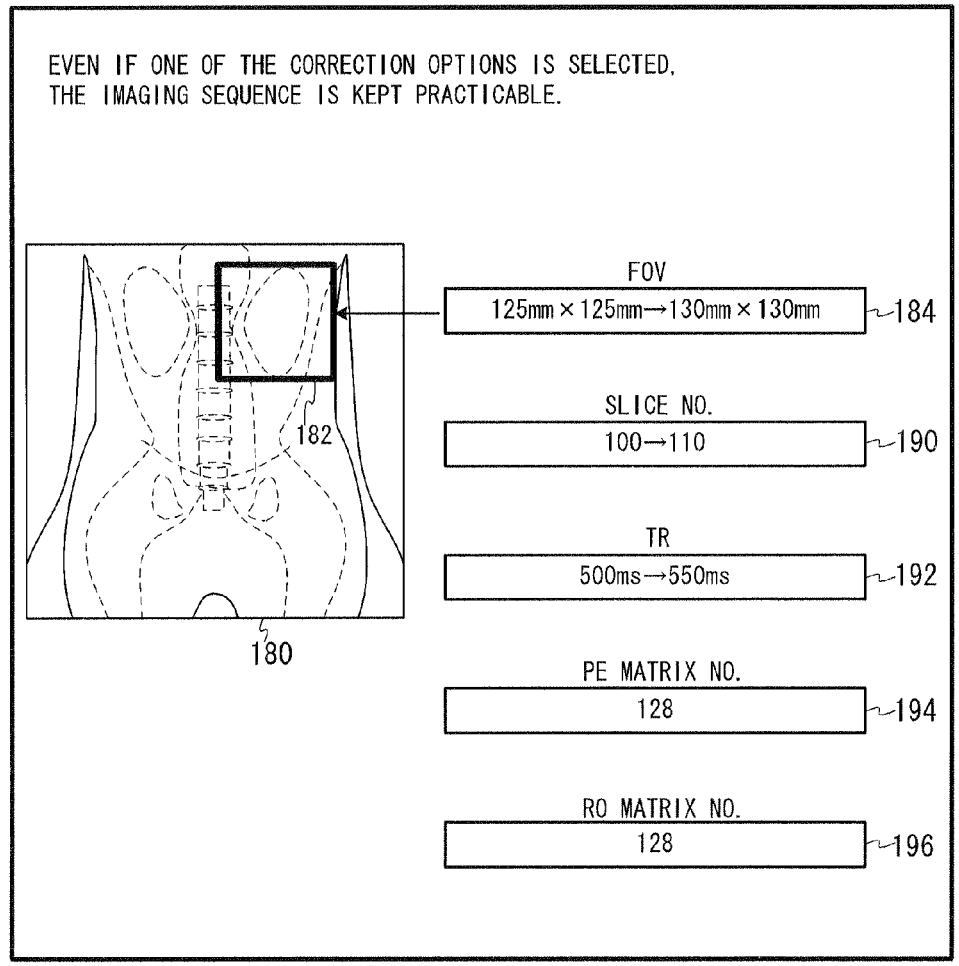
FIG. 16 is a schematic diagram showing an example of the display of correction options of imaging conditions, when a total electric load has a large margin as compared with an acceptable maximum electric load.

FIG. 16 is a schematic diagram showing an example of display of the correction options of imaging conditions, when a total electric load Lt has a large margin as compared with the maximum electric load Lmax. There is a possibility that a user selected conditions requiring less amount of the electric load in order for the total electric load Lt to unfailingly fall below the maximum electric load Lmax when the user first set imaging conditions.

In this case, there is a room for optimizing imaging conditions by the margin between the total electric load Lt and the maximum electric load Lmax. Then, in the present embodiment, when the total electric load Lt has considerable degree of margin as compared with the maximum electric load Lmax, correction options of imaging conditions which make the total electric load Lt closer to the maximum electric load Lmax are calculated and displayed as an example. The method of calculating these correction options will be explained in details in the after-mentioned step S8 in FIG. 17.

In the example of FIG. 16, the following three are displayed as the correction options of imaging conditions.

Firstly, to widen FOV to 130 mm×130 mm is displayed in the box 184 as one of the correction options.

Secondly, to increase the slice number to 110 is displayed in the box 190 as one of the correction options.

Thirdly, to lengthen the repetition time TR to 550 ms is displayed in the box 192 as one of the correction options.

A user can make the imaging conditions closer to more optimized conditions only by selecting one of those three correction options.

Figure 17:
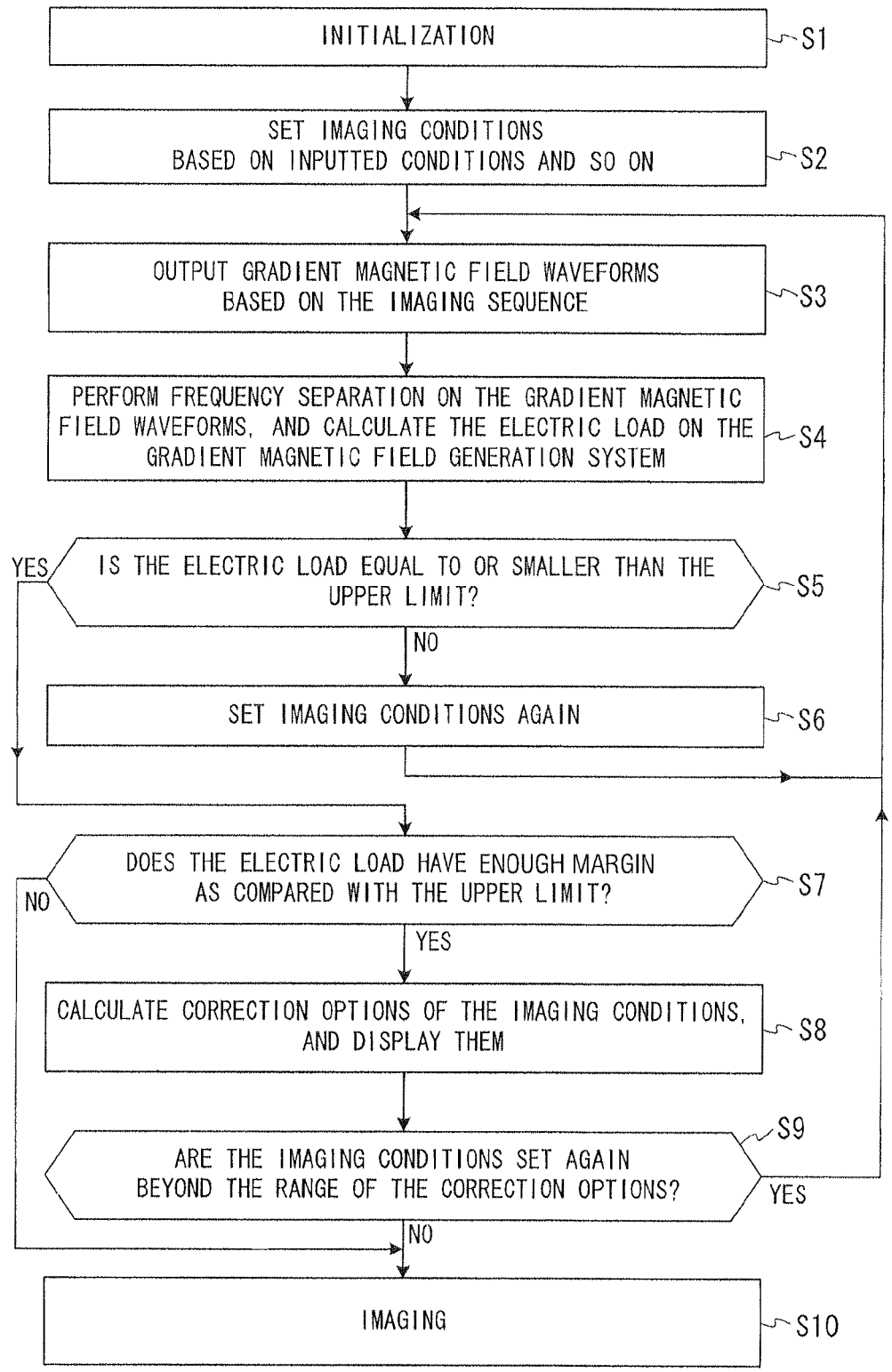
FIG. 17 is a flowchart illustrating a flow of a process performed by the MRI apparatus of the first embodiment.

FIG. 17 is a flowchart illustrating a flow of a process performed by the MRI apparatus 20 of the first embodiment. In the following, according to the step numbers in the flowchart shown in FIG. 17, an operation of the MRI apparatus 20 will be described by referring to the aforementioned respective drawings as required.

[Step S1] The MPU 86 (see FIG. 2) performs initial setting of the MRI apparatus 20 based on "a portion of imaging conditions or the like (input information)" inputted via the input device 62. Additionally, the center frequency of RF pulses and so on are set by a prescan and other means. After this, the process proceeds to Step S2.

[Step S2] The condition setting unit 100 provisionally sets the entire imaging conditions based on a portion of imaging conditions or the like inputted via the input device 62. That is, the condition setting unit 100 provisionally sets the imaging sequence of the main scan (including an application sequence of the gradient magnetic fields in the slice selection direction, the phase encode direction and the readout direction, and an application sequence of RF pulses: see FIG. 5 and FIG. 6). After this, the process proceeds to Step S3.

[Step S3] The waveform output unit 102 calculates the gradient magnetic field waveforms (time variation of gradient magnetic field intensity) of the X channel, the Y channel and the Z channel based on the imaging sequence, and outputs the calculated waveforms. The load acquisition unit 104 acquires data of the gradient magnetic field waveforms of each channel from the waveform output unit 102. After this, the process proceeds to Step S4.

[Step S4] The load acquisition unit 104 sets the separation number for frequency separation according to conditions such as a span of the imaging sequence and so on, in such a manner that calculation time for the electric load does not excesses a predetermined time. Additionally, the load acquisition unit 104 calculates the maximum frequency Fmax of the imaging sequence based on conditions of the imaging sequence.

Next, the load acquisition unit 104 determines each range of each frequency band for performing the frequency separation on the gradient magnetic field waveforms of the X channel, based on the frequency characteristics of impedance of the X axis gradient magnetic field coil 26x and the maximum frequency Fmax. For example, the frequency separation is performed, in such a manner that "respective differences between the maximum impedance and the minimum impedance of the respective frequency band" become mutually equal.

Note that, because many patterns of methods of frequency separation are preliminarily stored in the load acquisition unit 104, the load acquisition unit 104 selects one of the patterns. Thereby, the load coefficients groups stored in the load acquisition unit 104 as table data applicable to methods of performing frequency separation can be directly used for the calculation of the electric load without change.

The load acquisition unit 104 determines each range of each frequency band for performing frequency separation on the gradient magnetic field waveforms of the Y channel and the Z channel.

Next, the load acquisition unit 104 performs frequency separation on the gradient magnetic field waveforms of the respective X, Y and Z channels according to respective ranges determined in the aforementioned manner (see FIG. 7 to FIG. 12).

Next, the load acquisition unit 104 calculates the total electric load Lt imposed on the gradient magnetic field generation system in the provisionally set imaging sequence. That is, the load acquisition unit 104 calculates the X channel electric load Lx by using the load coefficients groups respectively corresponding to separated frequency bands. The load acquisition unit 104 calculates the Y channel electric load Ly and the Z channel electric load Lz in the same manner. Then, the load acquisition unit 104 sums up the X channel electric load Lx, the Y channel electric load Ly and the Z channel electric load Lz, as the total electric load Lt. Details of this calculation method have been previously explained, and overlapping explanation is abbreviated. After this, the process proceeds to Step S5.

[Step S5] The load acquisition unit 104 judges whether the total electric load Lt calculated in step S4 is equal to or smaller than the maximum electric load Lmax acceptable to the gradient magnetic field generation system or not.

When the total electric load Lt is equal to or smaller than the maximum electric load Lmax, the process proceeds to Step S7, because the provisionally set imaging sequence is practicable.

When the total electric load Lt excesses the maximum electric load Lmax, the process proceeds to Step S6, because the provisionally set imaging sequence is impracticable.

[Step S6] The load acquisition unit 104 inputs the resetting command of imaging conditions and the calculation result of the total electric load Lt to the condition setting unit 100. The condition setting unit 100 calculates a plurality of correction options of imaging conditions, in such a manner that the (total) electric load on the gradient magnetic field generation system in the case of performing the imaging sequence defined by reconfigured imaging conditions as magnetic resonance imaging does not exceed the maximum electric load Lmax.

Concretely speaking, for example, the condition setting unit 100 calculates how much percentage the inputted total electric load Lt overruns the maximum electric load Lmax, under the assumption that the maximum electric load Lmax is 100%. The condition setting unit 100 calculates a plurality of correction options of imaging conditions according to the calculated excess amount so as to decrease the electric load. Concretely speaking, the electric load becomes smaller by decreasing the slice number, lengthening the repetition time TR, decreasing the application amount of MPG (b-factor), expanding FOV and so on.

The condition setting unit 100 makes the display device 64 displays the plurality of the calculated correction options of the imaging conditions, by inputting them to the display control unit 98 (see FIG. 14).

The condition setting unit 100 automatically selects one of the plurality of correction options, if there is not selection operation by a user or input for setting imaging conditions again after elapse of a predetermined time span from the beginning time of displaying the correction options of imaging conditions. The priority order of the aforementioned automatic selection is, for example, to place the top priority on decreasing the slice number, and the priority order may be preliminarily set in step S1.

Note that, as explained with the aforementioned FIG. 15, imaging conditions may be automatically set (again) to the correction options and these correction options may be displayed. When a portion of imaging conditions are manually altered by a user after the above automatic resetting so as to increase the electric load, at least a portion of other conditions is automatically altered (set again) in tandem with the manual alteration of conditions.

As just described, one of the plurality of correction options is selected or imaging conditions are set again by manual operation of a user. The condition setting unit 100 defines (stipulates) an imaging sequence based on the imaging conditions which are set again as described above. After this, the process returns to step S3, and the total electric load Lt is calculated again.

[Step S7] The MPU 86 acquires the calculated total electric load Lt from the load acquisition unit 104. The MPU 86 judges whether or not the total electric load Lt has a predetermined proportion (ratio) of a margin or more as compared with the maximum electric load Lmax (i.e. the MPU 86 judges whether or not the total electric load Lt falls below the maximum electric load Lmax by a predetermined proportion of margin). The above predetermined proportion may be preliminarily set in the MPU 86 via the input device 62 in the step S1, for example.

More specifically, when the total electric load Lt is smaller than, for example, 70% (or 50% or 60%) of the maximum electric load Lmax, the MPU 86 judges that this case has an enough margin (room). Note that, the above numbers (70%, 50%, 60%) are only examples for concretizing explanation.

If the MPU 86 judges that this case has an enough margin, the process proceeds to step S8, and if this is not the case, the process proceeds to step S10.

[Step S8] The MPU 86 inputs the calculation command of correction options of at least a portion of imaging conditions to the condition setting unit 100 (i.e. the MPU 86 functions as an optimization command unit). The condition setting unit 100 calculates a plurality of correction options of imaging conditions in such a manner that the total electric load Lt gets closer to the maximum electric load Lmax.

More specifically, the condition setting unit 100 calculates the plurality of correction options of imaging conditions according to how much percentage the difference between the total electric load Lt and the maximum electric load Lmax is under the assumption that the maximum electric load Lmax is 100%.

The condition setting unit 100 calculates a plurality of correction options of imaging conditions according to the above margin, in such a manner that the total electric load Lt becomes larger and equal to a predetermined ratio (for example, a value which is equal to or smaller than 100% such as 85%) of the maximum electric load Lmax. Concretely speaking, the electric load becomes larger by increasing the slice number, increasing the application amount of MPG (b-factor), narrowing FOV and so on.

That is, there is a possibility that a user selected imaging conditions in such a manner that the total electric load Lt unfailingly falls below the maximum electric load Lmax when the user set imaging conditions in the step 1. In this case, there may be a room as compared with the maximum electric load Lmax by, for example, the slice number having been set to a too small value. Even in such a case, imaging conditions are optimized within the maximum electric load Lmax by performing the processing of step S7, S8 and S9.

The condition setting unit 100 makes the display device 64 display the calculated plurality of correction options of imaging conditions by inputting them to the display control unit 98 (see FIG. 16).

The condition setting unit 100 does not set imaging conditions once again, when there is not selective operation by a user or input for setting imaging conditions again during a predetermined time span from the beginning time of displaying the correction options of imaging conditions.

Note that, the condition setting unit 100 may automatically select one of the plurality of correction options, when there is not a selective operation by a user or input for setting imaging conditions again after elapse of the predetermined time span.

The priority order of the aforementioned automatic selection is, for example, to place the top priority on increasing the slice number, and the priority order may be preliminarily set in the step S1. After this, the process proceeds to step S9.

[Step S9] The MPU 86 judges whether the imaging conditions have been set again by a user to conditions beyond the range of the correction options calculated in the step S8 or not. If the imaging conditions have been set again to conditions beyond the range of the correction options, the process returns to step S3. If this is not the case, the process proceeds to step S10.

More specifically, for example, assume that slice number: 150 was displayed in the step S8 as one of the correction options of the imaging conditions. When the slice number is set again to a value equal to or less than 150 and other conditions are not changed, it is determined (judged) that the updated imaging conditions do not exceed correction options in terms of electric load.

Additionally, when one of the correction options of imaging conditions displayed in the step S8 is selected, it is determined that the updated imaging conditions do not exceed correction options. Additionally, when the imaging conditions are not changed, it is determined that the current imaging conditions do not exceed correction options.

On the other hand, when the slice number is set again to a value equal to or larger than 151, it is determined (judged) that the updated imaging conditions exceed correction options. Alternatively, when the FOV is set again to a range narrower than the range displayed as a correction option, it is determined that the updated imaging conditions exceed correction options. This is because there is possibility that the electric load exceeds the maximum electric load Lmax.

[Step S10] Data acquisition is performed according to the set imaging sequence.

More specifically, the object P is set on the bed 32 and a static magnetic field is formed in the imaging space by the static magnetic field magnet excited by the static magnetic field power supply 40. In addition, electric current is supplied from the shim coil power supply 42 to the shim coil 24, and thereby the static magnetic field formed in the imaging space is uniformed.

Then, when the MPU 86 receives a command of start of imaging from the input device 62, the MPU 86 inputs imaging sequence set by the condition setting unit 100 into the sequence controller 56. The sequence controller 56 drives the gradient magnetic field power supply 44, the RF transmitter 46 and the RF receiver 48 according to the inputted imaging sequence, thereby gradient magnetic fields are formed in the imaging region, and RF signals are generated from the RF coil 28.

Then, MR signals generated by nuclear magnetic resonance inside the object P are received by the RF coil 28 and detected by the RF receiver 48. The RF receiver 48 performs predetermined signal processing on the detected MR signals and then performs A/D conversion on the MR signals to generate raw data, which are digital data of the MR signals. The RF receiver 48 inputs the generated raw data to the sequence controller 56.

The sequence controller 56 inputs the raw data to the image reconstruction unit 90.

The image reconstruction unit 90 arranges the raw data in the k-space formed in the k-space database 92 as k-space data.

The image reconstruction unit 90 obtains the k-space data from the k-space database 92 and reconstructs image data by performing image reconstruction processing including 2-dimensional Fourier transformation on the obtained k-space data. The image reconstruction unit 90 stores the reconstructed image data in the image database 94.

The image processing unit 96 obtains the image data from the image database 94 and generates image data for 2-dimensional display by performing predetermined image processing on the obtained image data. The image processing unit 96 stores the image data for 2-dimensional display in the storage device 66.

Note that, an example has been described in which the condition setting unit 100 calculates the correction options of imaging conditions in the step S6 corresponding to the case of imaging sequence judged impracticable. However, calculation of the correction options is not indispensable. The MRI apparatus 20 may be configured to prompt a user to manually set imaging conditions again by displaying a caution notice on the display device 64 like in FIG. 13, without calculating the correction options.

The foregoing is a description of an operation of the MRI apparatus 20 according to the present embodiment.

As described above, in the first embodiment, the electric load of one channel is calculated by separating gradient magnetic field waveforms into a plurality of frequency bands depending on the frequency characteristic of impedance of the gradient magnetic field coil 26, calculating the electric load per frequency band and summing up them. This calculation is performed on each of the X, Y and Z channels, and the respective electric loads of the three channels are summed up. Therefore, the total electric load Lt on the gradient magnetic field generation system can be precisely calculated.

Because the total electric load Lt on the gradient magnetic field generation system can be precisely calculated, the MRI apparatus 20 can accurately determine whether there is an enough margin as compared with the acceptable maximum electric load Lmax or not, as well as the amount of the margin.

When the total electric load Lt has an enough margin up to the maximum electric load Lmax, the plurality of correction options of imaging conditions which make the total electric load Lt get closer to the maximum electric load Lmax are displayed. Thus, a user can optimize imaging conditions only by selecting one of the correction options.

On the other hand, when the total electric load Lt exceeds the maximum electric load Lmax, the imaging conditions are set again in such a manner that the total electric load Lt falls within the maximum electric load Lmax, and thus, the MRI apparatus 20 can be safely operated. As to the resetting of the imaging conditions, the plurality of correction options of imaging conditions are displayed. Thus, a user has only to select one of them. As a result, user-friendliness is improved.

That is, because the total electric load Lt is exactly calculated and then imaging conditions are set in such a manner that the total electric load Lt becomes equal to or less than the maximum electric load Lmax, it is able to optimize imaging conditions within the application limit of the gradient magnetic field generation system in terms of electric power.

The foregoing control of optimization is performed by calculation with the use of the preliminarily stored load coefficients and the frequency characteristic of impedance of the gradient magnetic field coil 26. So there is no additional component as compared with the conventional configuration in terms of hardware. That is, imaging conditions can be optimized without increasing cost of finished products.

Additionally, even if the gradient magnetic field coil 26 is replaced by, for example, repair, the aforementioned operation of the MRI apparatus 20 can be satisfied by updating the information stored in the load acquisition unit 104 such as the load coefficients and the frequency characteristic of impedance of the gradient magnetic field coil 26. That is, as to refurbishment of the gradient magnetic field generation system, its maintenance is easy.

According to the aforementioned embodiment, the electric load on the gradient magnetic field generation system of MRI can be precisely estimated depending on an imaging sequence.

Note that the electric load on the gradient magnetic field generation system cannot be accurately calculated in conventional technology. This is because it is not considered in the conventional technology that impedance of gradient magnetic field coils varies depending on frequency. Therefore, there is a margin beyond necessity between the application limit of the gradient magnetic field generation system in terms of electric power and the electric load of a pulse sequence which can be actually set in the conventional technology, and thus the conventional technology cannot optimize imaging conditions as sufficiently as the present embodiment.

The Second Embodiment

The second embodiment is a supplementary embodiment of the first embodiment, and the hardware configuration of the MRI apparatus 20 is the same as the first embodiment (see FIG. 1 and FIG. 2). The difference between the first embodiment and the second embodiment is the calculation method of the electric load only.

More specifically, the load coefficients in the first embodiment are determined by simulation or actual measurement, and the total electric load Lt calculated by using these load coefficients precisely gives the actual electric load value imposed on the gradient magnetic field generation system.

On the other hand, in the second embodiment, the total electric load Lt is calculated as a value larger than the actual electric load value imposed on the gradient magnetic field generation system. Thereby, the margin between the acceptable maximum electric load Lmax and the actual electric load on the gradient magnetic field generation system is always kept larger than a predetermined proportion (ratio), and the MRI apparatus 20 is safely operated.

As the first concrete method, the load acquisition unit 104 uses the load coefficients whose values are respectively larger than the load coefficients in the first embodiment by, for example, 1.2 times. The above magnification ratio of 1.2 is only an example for concretizing the explanation and does not limit the present embodiment, except that the magnification ratio should be larger than 1. As to the after-mentioned values, they are only examples for concretizing the explanation and do not limit the present embodiment. In this first concrete method, except the difference in the load coefficients, the calculation method of the total electric load Lt is the same as the first embodiment.

As the second concrete method, though the load acquisition unit 104 uses the same load coefficients as the first embodiment, the load acquisition unit 104 calculates the total electric load Lt by the following equation (3).

$$Lt=(Lx+Ly+Lz) \times W \quad (3)$$

Although the total electric load Lt is calculated by Lt=Lx+Ly+Lz in the first embodiment, the coefficient W in the equation (3) is a value larger than 1 and for example, W is 1.2. In this case, each calculation method of the X channel electric load Lx, the Y channel electric load Ly and the Z channel electric load Lz is the same as the first embodiment.

Note that this calculation method of the total electric load Lt is equivalent to the following calculation method in which the following equation (4) is used and the coefficient W' is larger than 0 and smaller than 1.

$$Lt=(Lx+Ly+Lz)/W' \quad (4)$$

As the third concrete method, though the load acquisition unit 104 uses the same load coefficients as the first embodiment, the load acquisition unit 104 calculates the total electric load Lt by using the following equation (5).

$$Lt=Lx+Ly+Lz+L\text{margin} \quad (5)$$

In the equation (5), the addition constant Lmargin is, for example, a value which is 20% of the maximum electric load Lmax. In this case, each calculation method of the X channel electric load Lx the Y channel electric load Ly and the Z channel electric load Lz is the same as the first embodiment.

Figure 18:
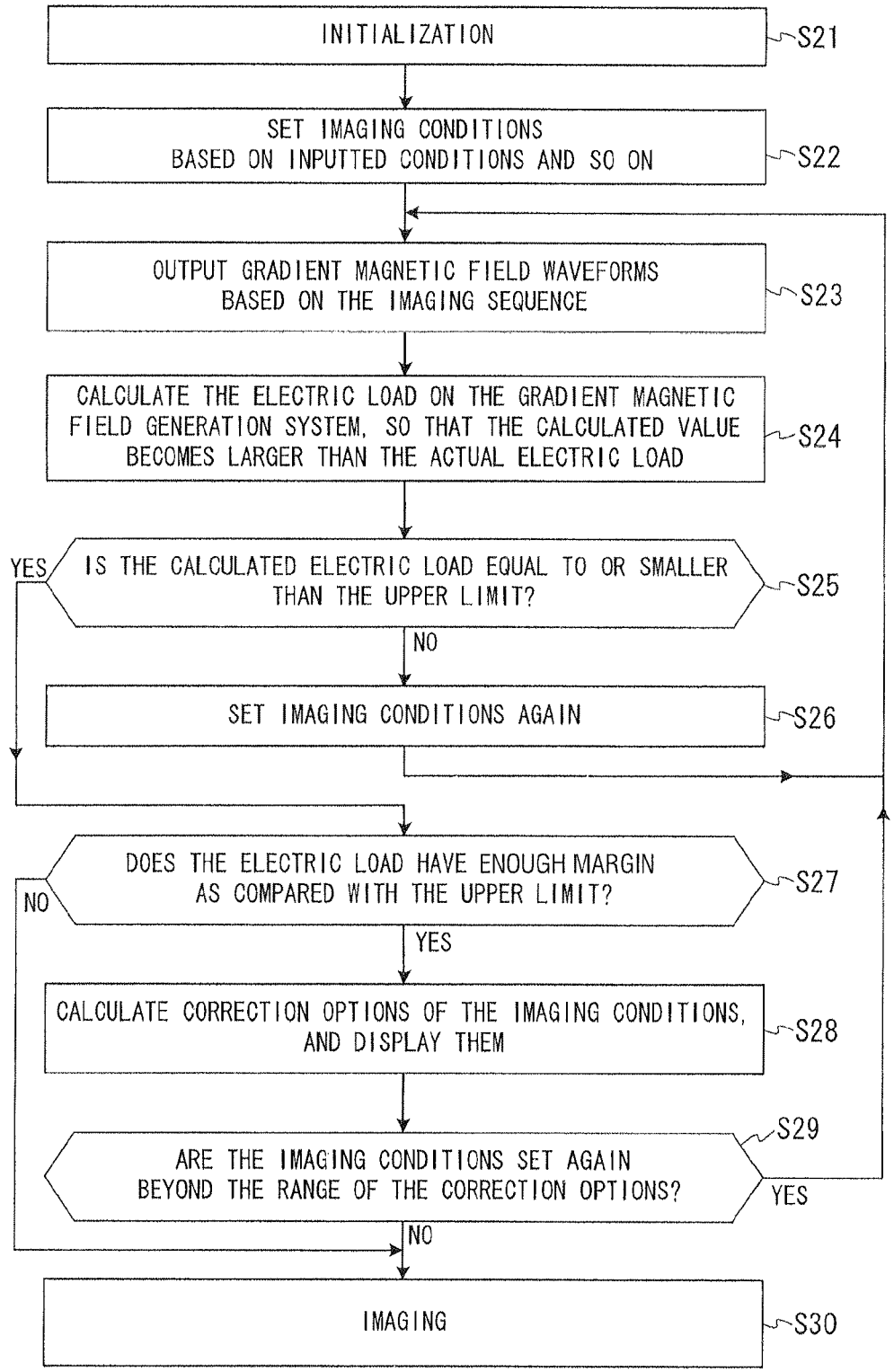
FIG. 18 is a flowchart illustrating a flow of a process performed by the MRI apparatus of the second embodiment.

FIG. 18 is a flowchart illustrating a flow of a process performed by the MRI apparatus 20 of the second embodiment. In the following, according to the step numbers in the flowchart shown in FIG. 18, an operation of the MRI apparatus 20 will be described.

[Steps S21 to S23] The steps S21 to S23 are respectively the same as the steps S1 to S3 in the first embodiment, and overlapping explanation is abbreviated.

[Step S24] The load acquisition unit 104 calculates the total electric load Lt by using one of the aforementioned methods, in such a manner that the calculated result becomes larger than the electric load actually imposed on the gradient magnetic field generation system. After this, the process proceeds to the step S25.

[Steps S25 to S30] The steps S25 to S30 are respectively the same as the steps S5 to S10 in the first embodiment, and overlapping explanation is abbreviated. The foregoing is the explanation of the operation of the MRI apparatus 20 of the second embodiment.

As described above, the effects similar to the first embodiment can be obtained in the second embodiment, too. Moreover, in the second embodiment, the total electric load Lt calculated so as to become larger than the actual value is compared with the maximum electric load Lmax acceptable to the gradient magnetic field generation system (in the step S25).

Thus, no matter how imaging conditions are set, the imaging conditions are set again as required in such a manner that the total electric load Lt calculated as a value larger than the actual electric load value becomes equal to or less than the maximum electric load Lmax (in the step S26).

Therefore, an electric load which is very close to application limit is never imposed on the gradient magnetic field generation system, and a margin from the admissible maximum electric load Lmax is always kept equal to or larger than a certain proportion. Thus, the MRI apparatus 20 can be extremely safely operated.

(Supplementary Notes on Embodiment)

[1] In the aforementioned embodiments, there has been described an example in which the values corresponding to square of electric current are used as the power duties in the calculation process of the total electric load Lt by squaring each value of the vertical axis of each chart of the gradient magnetic field waveforms. However, embodiments of the present invention are not limited to such an aspect.

Each absolute value of the vertical axis of the gradient magnetic field waveforms may be used as the power duty according to heating characteristics of an IGBT (Insulated Gate Bipolar Transistor) which is a switching device in the gradient magnetic field power supply 44. The power duty in this case corresponds to an absolute value of electric current. This is because instantaneous heating characteristics of an IGBT sometimes depend on amplitude of electric current, not square of electric current.

[2] There has been described an example in which respective separation numbers of frequency separation of the X channel, the Y channel and the Z channel are the same. However, embodiments of the present invention are not limited to such an aspect.

The total electric load Lt may be calculated by varying the separation number of frequency separation from channel to channel in the X channel, the Y channel and the Z channel, according to respective frequency characteristic of impedance of the X axis, the Y axis and the Z axis gradient magnetic field coils 26x, 26y and 26z.

[3] In the first embodiment, processing of the steps S7 to S9 for optimizing the imaging conditions is not indispensable, and may be abbreviated. That is, if the judgment result in the step S5 is practicable (affirmative), the process may proceed to the step S10. The same applies to the second embodiment.

[4] In the first and second embodiments, there has been described an example in which waveforms of the gradient magnetic fields are separated into a plurality of frequency bands, respective electric loads on the gradient magnetic field generation system are calculated per frequency band and these electric loads are summed up. However, embodiments of the present invention are not limited to such an aspect.

Information on a waveform of a gradient magnetic field such as coordinate data stipulating a gradient magnetic field waveform may be used instead of waveforms themselves of the gradient magnetic fields.

Figure 19:
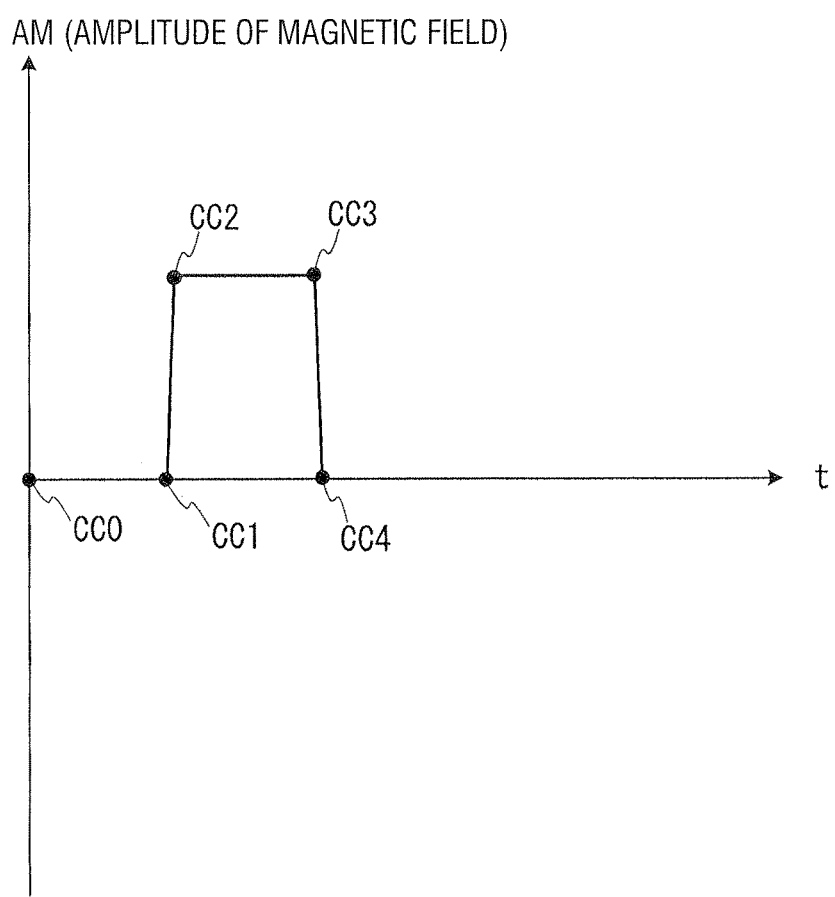
FIG. 19 is a schematic diagram showing an example of coordinate data which duplicate gradient magnetic field waveforms.

FIG. 19 is a schematic diagram showing an example of coordinate data which duplicate gradient magnetic field waveforms. In FIG. 19, the abscissa axis indicates elapsed time t from the starting time of an imaging sequence (t=0 second), and the vertical axis indicates gradient magnetic field intensity AM.

In this example, the waveform of an MPG pulse is defined by five coordinate points from the starting time of the imaging sequence.

That is, the coordinate point CC0 indicates, for example, elapsed time t=0 and gradient magnetic field intensity AM=0.

The coordinate point CC1 indicates, for example, t=0.01 and AM=0, for example.

The coordinate point CC2 indicates, for example, t=0.0101 and AM=1

The coordinate point CC3 indicates, for example, t=0.02 and AM=1

The coordinate point CC4 indicates, for example, t=0.0201 and AM=0.

As described above, each gradient magnetic field waveform of the gradient magnetic field Gx in the X axis direction, the gradient magnetic field Gy in the Y axis direction and the gradient magnetic field Gz in the Z axis direction can be defined based on many coordinate values. In this case, the load acquisition unit 104 acquires coordinate data stipulating (defining) gradient magnetic field waveforms from the waveform output unit 102, and can calculate each electric load on the gradient magnetic field generation system per separated frequency band based on the coordinate data, in the way similar to the aforementioned embodiments.

[5] In the first and second embodiments, there has been described an example in which the total electric load Lt on the gradient magnetic field generation system is calculated after provisionally setting imaging conditions before performance of the imaging sequence defined by the imaging conditions. However, embodiments of the present invention are not limited to such an aspect but include the following supplementary embodiment.

Many of representative patterns of imaging conditions such as a form of a pulse sequence and each parameter value of each condition may be preliminarily made out, and these patterns may be preliminarily stored (before shipment of the MRI apparatus 20, for example). That is, each pattern is a set of conditions defining one imaging sequence. In this case, each of the total electric loads Lt calculated for the imaging sequences of the respective patterns is stored in the load acquisition unit 104.

Specifically, for example, the load acquisition unit 104 stores the imaging conditions of each pattern and each of the total electric loads Lt in the case of performing the imaging sequence defined by the imaging conditions of each pattern, as table data.

The table data is also information stipulating relationship between imaging conditions and the electric load on the gradient magnetic field generation system, according to the frequency characteristic of impedance of the gradient magnetic field coil 26. The calculation method of the preliminarily stored total electric loads Lt is the same as the calculation method of the total electric load Lt in the first embodiment.

The operation of the MRI apparatus 20 in this case is the same as the first and second embodiments, except that the following processing is performed instead of the processing in the steps S3 and S4 in FIG. 17 (or the steps S23 and S24 in FIG. 18).

That is, the load acquisition unit 104 selects the pattern closest to the currently set imaging conditions, out of the stored data. The load acquisition unit 104 acquires the total electric load Lt stored for (corresponding to) the selected pattern.

In this case, after setting imaging conditions, the total electric load Lt on the gradient magnetic field generation system can be obtained only by reading out the stored data, without performing arithmetic processing. Thus, calculation time of computer 58 can be abbreviated and time required for setting imaging conditions can be shortened.

Note that both of (A) the embodiment in which the electric loads are preliminarily stored for various patterns of imaging conditions respectively and (B) the first and second embodiments in which the electric load is calculated each time imaging conditions are set are based on the following concept.

Specifically, three steps of (1) provisional setting or resetting of imaging conditions, (2) acquisition of the electric load in the case of performing the imaging sequence defined by the set imaging conditions, (3) judgment as to whether the set imaging sequence is practicable or not, are repeated.

These three steps are sequentially repeated until the set imaging sequence is judged practicable in the aforementioned (3) and the imaging conditions are finally fixed.

In other words, imaging conditions and the electric load in the case of performing the imaging sequence are sequentially acquired and updated, until the imaging conditions are finally fixed.

[6] An example has been described in which the RF receiver 48 is disposed, as the MRI apparatus, 20, outside the gantry that includes the static magnetic field magnet 22, the shim coil 24, the gradient magnetic field coil unit 26, the RF coils 28 and the like (see FIG. 1). However, the embodiment of the present invention is not limited to such an implementation. The RF receiver 48 may be included in the gantry.

Specifically, for example, an electronic circuit board that is equivalent to the RF receiver 48 may be disposed in the gantry. Then, the MR signal, which is an analog electrical signal converted from the electromagnetic wave by the receiving RF coil 28, may be amplified by a pre-amplifier in the electronic circuit board, the amplified signal may be outputted to the outside of the gantry as a digital signal and inputted to the sequence controller 56. In outputting the signal to the outside of the gantry, for example, an optical communication cable is preferably used to transmit the signal in the form of an optical digital signal. This is because the effect of external noise is reduced.

[7] While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A magnetic resonance imaging apparatus performing magnetic resonance imaging under a gradient magnetic field by providing a gradient magnetic field generation system with electric current to apply the gradient magnetic field on an imaging region, comprising:

a condition setting unit configured to set imaging conditions of the magnetic resonance imaging; and a load acquisition unit configured to acquire information on a waveform of the gradient magnetic field and calculate respective electric loads for a plurality of frequency bands that would be imposed on the gradient magnetic field generation system for said set imaging conditions of magnetic resonance imaging, based on the information on a waveform.

2. The magnetic resonance imaging apparatus according to claim 1, wherein the load acquisition unit is configured to judge whether an imaging sequence defined by the imaging conditions set by the condition setting unit is practicable or not, based on the electric loads, and input a resetting command of imaging conditions to the condition setting unit in a case of judging the imaging sequence impracticable; and the condition setting unit is configured to set the imaging conditions again for updating based on the electric loads calculated by the load acquisition unit in a case of receiving the resetting command, so that a total of electric loads given by updated imaging conditions does not exceed a maximum load acceptable to the gradient magnetic field generation system.

3. The magnetic resonance imaging apparatus according to claim 2, wherein the load acquisition unit is configured to preliminarily store respective load coefficients for the plurality of frequency bands before performance of the magnetic resonance imaging, and calculate the respective electric loads for the plurality of frequency bands by multiplying electric quantity supplied to the gradient magnetic field generation system by each load coefficient corresponding to each frequency band.

4. The magnetic resonance imaging apparatus according to claim 3, wherein the gradient magnetic field generation system is a part of the magnetic resonance imaging apparatus and includes three gradient magnetic field coils each of which generates a gradient magnetic field in a predetermined direction mutually orthogonal to each other; and the load acquisition unit is configured to calculate respective electric loads on the gradient magnetic field coils per frequency band by multiplying electric quantity supplied to each of the gradient magnetic field coils by each load coefficient corresponding to each frequency band, calculate a total load by summing up the respective electric loads on the gradient magnetic field coils calculated per frequency band, and judge whether the imaging sequence is practicable or not based on the total load.

5. The magnetic resonance imaging apparatus according to claim 4, wherein the gradient magnetic field generation system further includes a gradient magnetic field power supply, cables connecting the three gradient magnetic field coils to the gradient magnetic field power supply respectively, and an EMC filter; and the load acquisition unit is configured to calculate a value of an electric load imposed on a whole of the gradient magnetic field generation system, as the total load.

6. The magnetic resonance imaging apparatus according to claim 5, further comprising a display device, wherein the condition setting unit is configured to calculate a correction option of at least a portion of imaging conditions in a case of receiving the resetting command, in such a manner that the total load does not exceed the maximum load; and the display device is configured to display the correction option.

7. The magnetic resonance imaging apparatus according to claim 6, further comprising an optimization command unit configured to judge whether the total load has a predetermined proportion of a margin below the maximum load or not, and input a calculation command of the correction option of at least a portion of imaging conditions to the condition setting unit in a case of judging that the total load has the predetermined proportion of a margin;

wherein the condition setting unit is configured to calculate the correction option so that the total load increases toward the maximum load and to make the display device display the correction option, in a case of receiving the calculation command from the optimization command unit.

8. The magnetic resonance imaging apparatus according to claim 3, wherein the condition setting unit is configured to calculate each of the electric loads as a lager value than a value of an actual electric load, by using a load coefficient which gives a value larger than a value of an electric load actually imposed on the gradient magnetic field generation system, multiplying a coefficient larger than 1 in a process of calculating the electric loads or adding a predetermined margin in a process of calculating the electric loads.

9. The magnetic resonance imaging apparatus according to claim 3, wherein the gradient magnetic field generation system is a part of the magnetic resonance imaging apparatus and includes a gradient magnetic field coil which generates the gradient magnetic field; and the load acquisition unit is configured to vary respective frequency bands according to frequency characteristics of impedance of the gradient magnetic field coil and perform frequency separation on the waveform of the gradient magnetic field based on varied frequency bands.

10. The magnetic resonance imaging apparatus according to claim 3, wherein the gradient magnetic field generation system further includes a gradient magnetic field coil, a gradient magnetic field power supply, a cable connecting the gradient magnetic field coil to the gradient magnetic field power supply, and an EMC filter; and the load acquisition unit is configured to calculate a value of an electric load imposed on a whole of the gradient magnetic field generation system, as a total of the electric loads.

11. The magnetic resonance imaging apparatus according to claim 1, further comprising a display device, wherein the load acquisition unit is configured to judge whether a total of the electric loads exceeds a maximum load acceptable to the gradient magnetic field generation system or not; and the display device is configured to display a notice indicating that the imaging sequence is impracticable, when a judgment result of the load acquisition unit is affirmative.

12. The magnetic resonance imaging apparatus according to claim 1, further comprising a display device, wherein the load acquisition unit is configured to judge whether a total of the electric loads exceeds a maximum load acceptable to the gradient magnetic field generation system or not;

the condition setting unit is configured to calculate a correction option of at least a portion of imaging conditions in such a manner that the total does not exceed the maximum load, when a judgment result of the load acquisition unit is affirmative; and the display device is configured to display the correction option.

13. The magnetic resonance imaging apparatus according to claim 12, wherein when a portion of imaging conditions is varied after display of the correction option on the display device, the condition setting unit calculates a correction option of a condition excluding a varied condition so that the total does not exceed the maximum load, and makes the display device display the correction option of a condition excluding a varied condition.

14. A magnetic resonance imaging apparatus performing magnetic resonance imaging under a gradient magnetic field by providing a gradient magnetic field generation system with electric current to apply the gradient magnetic field on an imaging region, comprising:

a condition setting unit configured to set imaging conditions of the magnetic resonance imaging; and a load acquisition unit configured to calculate an electric load on the gradient magnetic field generation system for said set imaging conditions of magnetic resonance imaging, based on information on frequency of a waveform of the gradient magnetic field, and output the electric load.

15. The magnetic resonance imaging apparatus according to claim 14, wherein the electric load on the gradient magnetic field generation system is a value obtained by summing up electric loads which are respectively calculated for a plurality of frequency bands.

16. The magnetic resonance imaging apparatus according to claim 15, wherein the load acquisition unit is configured to judge whether an imaging sequence defined by the imaging conditions is practicable or not, based on the electric load, and input a resetting command of imaging conditions to the condition setting unit in a case of judging that the imaging sequence is impracticable; and the condition setting unit is configured to set the imaging conditions again in a case of receiving the resetting command, so that the electric load does not exceed a maximum load acceptable to the gradient magnetic field generation system.

17. The magnetic resonance imaging apparatus according to claim 15, further comprising a display device, wherein the load acquisition unit is configured to judge whether the electric loads exceeds a maximum load acceptable to the gradient magnetic field generation system or not; and the display device is configured to display a notice indicating that an imaging sequence defined by the imaging conditions is impracticable, when a judgment result of the load acquisition unit is affirmative.

18. The magnetic resonance imaging apparatus according to claim 15, further comprising a display device, wherein the load acquisition unit is configured to judge whether the electric load exceeds a maximum load acceptable to the gradient magnetic field generation system or not;

the condition setting unit is configured to calculate a correction option of at least a portion of imaging conditions in such a manner that the electric load does not exceed the maximum load, when a judgment result of the load acquisition unit is affirmative; and the display device is configured to display the correction option.

19. A load calculation method for a gradient magnetic field generation system in a magnetic resonance imaging (MRI) system, said method comprising:

configuring at least one computer in an MRI system to set imaging conditions of magnetic resonance imaging under a gradient magnetic field applied by a gradient magnetic field generation system;

calculate an electric load on the gradient magnetic field generation system if the magnetic resonance imaging was to be performed based on the imaging conditions; and control the MRI system not to perform the magnetic resonance imaging based on the set imaging conditions if the calculated electric load exceeds a predetermined electric load.

* * * * *